US006300472B1

(12) United States Patent
Hillman et al.

(10) Patent No.: US 6,300,472 B1
(45) Date of Patent: Oct. 9, 2001

(54) RAB PROTEINS

(75) Inventors: Jennifer L. Hillman, Mountain View; Preeti Lal, Santa Clara; Neil C. Corley, Mountain View; Purvi Shah, Sunnyvale, all of CA (US)

(73) Assignee: Incyte Genomics, Inc., Palo Alto, CA (US)

( * ) Notice: Subject to any disclaimer, the term of this patent is extended or adjusted under 35 U.S.C. 154(b) by 0 days.

(21) Appl. No.: 09/154,602

(22) Filed: Sep. 16, 1998

Related U.S. Application Data

(62) Division of application No. 08/916,901, filed on Aug. 21, 1997, now Pat. No. 5,892,012.

(51) Int. Cl.⁷ ..................................................... C07K 1/00
(52) U.S. Cl. .................. 530/350; 530/387.1; 530/387.9; 530/389.1; 514/12
(58) Field of Search ................................ 530/350, 287.1, 530/287.9, 289.1; 514/12

(56) References Cited

PUBLICATIONS

Bork, Genome Research vol. 10, p. 398, 2000.*
Novick, P. and P. Brenwald, "Friends and Family: The Role of the Rab GTPases in Vesicular Traffic", *Cell*, 75: 597–601 (1993).
Khosravi–Far, R. et al., "Isoprenoid modification of rab proteins terminating in CC or CXC motifs", *Proc. Natl. Acad. Sci. USA*, 88: 6264–6268 (1991).
Zahraoui, A., et al., "The Human Rab Genes Encode a Family of GTP–binding Proteins Related to Yeast YPT1 and SEC4 Products Invovled in Secretion", *J. Biol. Chem.*, 264: 12394–12401 (1989).
Brauers, A. et al., "Alternative mRNA splicing of the novel GTPase Rab28 generates isoforms with different C–termini", *Eur. J. Biochem.*, 237: 833–840 (1996) (GI 1154900; GI 1154901).
Olkkonen, V.M. et al., "Molecular cloning and subcellular localization of three GTP–binding proteins of the rab subfamily", *J. Cell Sci.*, 106: 1249–1261 (1993) (GI 438163; GI 438164).
Fridell, R.A. et al., "Nuclear export of late HIV–1 mRNAs occurs via a cellular protein export pathway", *Proc. Natl. Acad. Sci. USA*, 93: 4421–4424 (1996).
Seabra, M.C. et al., "Retinal Degeneration in Chloroderemia: Deficiency of Rab Geranylgeranyl Transferase", *Science*, 259: 377–381 (1993).
Tuomikoski, T. et al., "Inhibition of endocytic vesicle fusion in vitro by the cell–cycle control protein kinase cdc2", *Nature*, 342: 942–945 (1989).
Vielh, E. et al., "Nucleotide sequence of a rat cDNA: RAB1B, encoding a RAB1–YPT related protein", *Nucl. Acids Res.*, 17: 1770 (1989) (GI 57005; GI 57006).
Ren, M. et al., "In its active form, the GTP–binding protein rab8 interacts with a stress–activated protein kinase", *Proc. Natl. Acad. Sci. USA*, 93: 5151–5155 (1996).
Swissprot Database Entry Rb24 Mouse, Acession No. P35290; Feb. 1, 1994.

* cited by examiner

*Primary Examiner*—Sheela Huff
(74) *Attorney, Agent, or Firm*—Incyte Genomics, Inc.

(57) ABSTRACT

The invention provides three human Rab proteins (RABP) and polynucleotides which identify and encode RABP. The invention also provides expression vectors, host cells, agonists, antibodies and antagonists. The invention also provides methods for treating disorders associated with expression of RABP.

6 Claims, 24 Drawing Sheets

```
       9          18         27         36         45         54
5' CCC ACG CGT CCG CGC GGC GCT GCG AGG AGC CGG GTT GCG GGA GAC CCC AGG 63         72         81         90         99        108
   TTC GGT TGG GAT TCC CAG CCA GAA CGG AGC TTA AGC CGG GCA GGC GAG CGA ATG 117        126        135        144        153        162
   ACG GAG TAG CGA GCT GCA CGG CGG CGT GCT GCG CTG TTG AGG ACG CTG TCC CGC 171        180        189        198        207        216
   GCC CTC CCA GGC CGC CCC GAG GCT TGG GGT CTT CGA AGG ATA ATC GGC GCC CGG 225        234        243        252        261        270
   GGC CGA ACA GCG GGG GCA CAC GGG GCG CTG CCG AAG TGC AAG GCC ACG GCC AGA 279        288        297        306        315        324
   GCT CGA GCC CGA CGC GCT GTC TGG AGT CGT AGG TTG GCG CCG TTT GGG GTC GGG 333        342        351        360        369        378
   GTC TGA GGC TTG GGC GCT GCC GAG CGG AGA TCG GGG TTT GCC TCC CGT
```

FIGURE 1A

```
     387            396            405            414            423            432
CCC CGC TCA GGA CCC TGA CGT GGC TGA AGC GGC CCC GGG AGC ATG AGC GGG CAG
                                                           M   S   G   Q 441            450            459            468            477            486
CGC GTG GAC GTC AAG GTG ATG GTG CTG GGC AAG GAG TAC GTG GGC AAG ACT AGC
 R   V   D   V   K   V   M   V   L   G   K   E   Y   V   G   K   T   S 495            504            513            522            531            540
CTG GTG GAG CGC TAC GTG CAC GNC TTT CTG GGG CCT TAT CAG AAC ACC
 L   V   E   R   Y   V   H   X   F   L   G   P   Y   Q   N   T 549            558            567            576            585            594
ATC GGG GCC GCG TTC GTG GCC AAG GTG ATG TCG GGA GAC GTC GGA ACT GTG ACA
 I   G   A   A   F   V   A   K   V   M   S   G   D   V   G   T   V   T 603            612            621            630            639            648
TTA GGT ATT TGG GAC ACA GCA GGC TCT GAG CGC TAT GAG GCC ATG AGT AGA ATC
 L   G   I   W   D   T   A   G   S   E   R   Y   E   A   M   S   R   I 657            666            675            684            693            702
TAC TAT CGG GGT GCC AAG GCT GCC ATC GTC TGC TAT GAC CTC ACA GAC AGC AGC
 Y   Y   R   G   A   K   A   A   I   V   C   Y   D   L   T   D   S   S 711            720            729            738            747            756
AGC TTT GAG CGA GCA AAG TTC TGG GTG AAG GAA CTG CGC AGC CTA GAG GAG GGC
 S   F   E   R   A   K   F   W   V   K   E   L   R   S   L   E   E   G
```

FIGURE 1B

```
      765                774           783           792           801           810
TGC CAA ATC TAC TTA TGT GGC ACC AAG AGT GAC CTG GAA GAC CGG AGG
 C   Q   I   Y   L   C   G   T   K   S   D   L   E   D   R   R 819                828           837           846           855           864
CGT CGA CGT GTG GAC TTC CAC GAC GTC CAG GAC TAT GCA GAC AAT ATC AAA GCT
 R   R   R   V   D   F   H   D   V   Q   D   Y   A   D   N   I   K   A 873                882           891           900           909           918
CAG CTC TTT GAA ACA TCC AGC AAG ACA GGC AGT GTG GAC GAG CTC TTC CAG
 Q   L   F   E   T   S   S   K   T   G   S   V   D   E   L   F   Q 927                936           945           954           963           972
AAA GTG GCA GAG GAT TAC GTC AGT GTG GCT GTC CAG TTC CAG GTG ATG ACA GAG GAC
 K   V   A   E   D   Y   V   S   V   A   V   Q   F   Q   V   M   T   E   D 981                990           999           1008          1017          1026
AAG GGC GTG GAT CTG GGC CAG AAG CCA AAC CCC TAC TTC TAC AGC TGT TGT CAT
 K   G   V   D   L   G   Q   K   P   N   P   Y   F   Y   S   C   C   H 1035               1044          1053          1062          1071          1080
CAC TGA GTC AGC ACT CAC CTG GCC CTG TGG GGG AAT TAA AGG AAT TCC CCG TAA GGG
 H 1089               1098          1107          1116          1125          1134
CTG GAC CCA GCT CCT TTC TGG GCT TGG GTA GTC AAA TGT CTG AGC TAC CCC AGG
```

FIGURE 1C

```
     1143      1152           1161           1170           1179           1188
TCC TCA TGT CAG CAG AGT GGC GCC TGC CTG TGC TGG CCC ATG GAA CGG AGA CAG 1197      1206           1215           1224           1233           1242
CAT TGG GCT GAC TGT GGG CAT GAG GAG GGA TAA GGC TGA TTT GGA CCC CAG GCT 1251      1260           1269           1278           1287           1296
TCT GCC CTG GAC AGC ACT TGT GTC TGC AGA TTA TTT AAG TGG CTT TTG ATC TGT 1305      1314           1323           1332
AAA TAA AAT CAG TGC ACT GTG AAT CAC AAA AAA AAA GG 3'
```

FIGURE 1D

```
                                                9           18          27          36          45          54
5' NAC CAT CTT GGA ACG GGA GGC GGA CAG AGT CGA CAG CTG GGA GCG ACC GAG CGG GCC 63          72          81          90          99         108
   GCC GCC GCC ATG AAC CCC GAA TAT GAC TAC CTG TTT AAG CTG TTG ATT
               M   N   P   E   Y   D   Y   L   F   K   L   L   I 117         126         135         144         153         162
   GGC GAC TCA GGC GTG AAG TCA TGC CTG CTC CTG CGG TTT GCT GAT GAC ACG
    G   D   S   G   V   K   S   C   L   L   L   R   F   A   D   D   T 171         180         189         198         207         216
   TAC ACA GAG AGC TAC ATC AGC ACC ATC GGG GTG GAC TTC AAG ATC CGA ACC ATC
    Y   T   E   S   Y   I   S   T   I   G   V   D   F   K   I   R   T   I 225         234         243         252         261         270
   GAG CTG GAT GGC AAA ACT ATC AAA CTT CAG ATC TGG GAC ACA GGC CAG GAA
    E   L   D   G   K   T   I   K   L   Q   I   W   D   T   A   G   Q   E 279         288         297         306         315         324
   CGG TTC CGG ACC ATC ACT TCC AGC TAC TAC CGG GGG GCT CAT GGC ATC ATC GTG
    R   F   R   T   I   T   S   S   Y   Y   R   G   A   H   G   I   I   V 333         342         351         360         369         378
   GTG TAT GAC GTC ACT GAC CAG GAA TCC TAC GCC AAC GTG AAG CAG TGG CTG CAG
    V   Y   D   V   T   D   Q   E   S   Y   A   N   V   K   Q   W   L   Q

FIGURE 2A
```

```
      387         396         405         414         423         432
GAG ATT GAC CGC TAT GCC AGC GAG AAC GTC AAT AAG CTC CTG GTG GGC AAC AAG
 E   I   D   R   Y   A   S   E   N   V   N   K   L   L   V   G   N   K 441         450         459         468         477         486
AGC GAC CTC ACC ACC AAG AAG GTG GAC AAC ACA GCC AAG GAG TTT GCA
 S   D   L   T   T   K   K   V   D   N   T   A   K   E   F   A 495         504         513         522         531         540
GAC TCT CTG GGC ATC CCC TTC TTG GAG ACG AGC GCC AAG AAT GCC ACC AAT GTC
 D   S   L   G   I   P   F   L   E   T   S   A   K   N   A   T   N   V 549         558         567         576         585         594
GAG CAG GCG TTC ATG ACC ATG GCT GAA ATC AAA AAG CGG ATG GGG CCT GGA
 E   Q   A   F   M   T   M   A   E   I   K   K   R   M   G   P   G 603         612         621         630         639         648
GCA GCC TCT GGG GGC GAG CGG CCC AAT CTC AAG ATC GAC AGC ACC CCT GTA AAG
 A   A   S   G   G   E   R   P   N   L   K   I   D   S   T   P   V   K 657         666         675         684         693         702
CCG GCT GGC GGT TGC TGT TGC TAG GAG GGG CAC ATG GAG TGG GAC AGG AGG GGG
 P   A   G   G   C   C   C   *

711         720         729         738         747         756
CAC CTT CAG ATG ATG TCC CTG GAG GGG GCA GGA GGT ACC TCC CTC TCC CTC
```

FIGURE 2B

```
              765        774        783        792        801        810
        TCC TGG GGC ATT TGA GTC TGT GGC TTT GGG GTG TCC TGG GCT CCC CAT CTC CTT 819        828        837        846        855        864
        CTG GCC CAT CTG CCT GCT GCT GCC CTG AGC CCC GGT TCT GTC AGG GTC CCT AAA GGA 873        882        891        900        909        918
        GGA CAC TCA GGG CCT GTG GCC AGG CAG GGC GGA AGC CTG CTG TGC TGT TGC CTC

TAG GTG AC 3'
```

FIGURE 2C

```
                                 9                18               27               36               45               54
5' GGG AGG TGG GCA AGA TGG CGC TTG CCG AGT GAT TCT CCT CGA ATA CCT CCT GCC 63               72               81               90               99              108
   GGC GCG GAG ACA CCG GAG GGG CGG GGG TCC TGC CGC AAC TAC CTC CCT TCC TCT 117              126              135              144              153              162
   CCC CCG CCG GAG CCT TCA TCC TTC CCT TCC CCC ACC TCG AGG GGC GGG 171              180              189              198              207              216
   CCT GGT TCC CGG GAC ACC ATG TCG GAC TCT GAG GAG GAG AGC CAG GAC CGG CAA
                                           M   S   D   S   E   E   E   S   Q   D   R   Q 225              234              243              252              261              270
   CTG AAA ATC GTC GTG CTG GGG GAC GGC GCC TCC GGG AAG ACC TCC TTA ACT ACG
   L   K   I   V   V   L   G   D   G   A   S   G   K   T   S   L   T   T 279              288              297              306              315              324
   TGT TTT GCT CAA GAA ACT TTT GGG AAA CAG TAC AAA CAA ACT ATA GGA CTG GAT
   C   F   A   Q   E   T   F   G   K   Q   Y   K   Q   T   I   G   L   D 333              342              351              360              369              378
   TTC TTG AGA AGG ATA ACA TTG CCA GGA AAC TTG AAT GTT ACC CTT CAA ATT
```

FIGURE 3A

```
       F   F   L   R   I   T   L   P   G   N   L   N   V   T   L   Q   I
                387         396         405         414         423         432
      TGG GAT ATA GGA GGG CAG ACA ATA GGA GGC AAA ATG TTG GAT AAA TAT ATC TAT
       W   D   I   G   G   Q   T   I   G   G   K   M   L   D   K   Y   I   Y
                441         450         459         468         477         486
      GGA GCA CAG GGA GTC CTC TTG GTA TAT GAT ATT ACA AAT TAT CAA AGC TTT GAG
       G   A   Q   G   V   L   L   V   Y   D   I   T   N   Y   Q   S   F   E
                495         504         513         522         531         540
      AAT TTA GAA GAT TGG TAT ACT GTG AAG AAA ATT GTG AAG AGC GAG TCA GAA ACT
       N   L   E   D   W   Y   T   V   K   K   I   V   K   S   E   S   E   T
                549         558         567         576         585         594
      CAG CCA CTG GTT GCC TTG GTA GGC AAT AAA ATT GAT TTG GAG CAT ATG CGA ACA
       Q   P   L   V   A   L   V   G   N   K   I   D   L   E   H   M   R   T
                603         612         621         630         639         648
      ATA AAA CCT GAA AAA CAC TTA CGG TTT TGC CAG GAA AAT GGT TTT AAT AGC CAC
       I   K   P   E   K   H   L   R   F   C   Q   E   N   G   F   N   S   H
                657         666         675         684         693         702
      TTT GTT TCA GCC AAG GCA AGA GAC TCT GTC TTC TGT TTT CAA AAA GTT GTT
       F   V   S   A   K   A   R   D   S   V   F   C   F   Q   K   V   V
```

FIGURE 3B

```
       711            720            729            738            747            756
GCT GAA ATC CTT GGA ATC AAA TTA AAC AAA GCA GAA ATA GAA CAG TCA CAG AGG
 A   E   I   L   G   I   K   L   N   K   A   E   I   E   Q   S   Q   R
              765            774            783            792   801            810
GTG GTA AAG GCA GAT ATT GTA AAC TAC AAC CAG GAA CCT ATG GCA AGA GCT GTT
 V   V   K   A   D   I   V   N   Y   N   Q   E   P   M   A   R   A   V
       819            828            837            846            855            864
AAC CCT TCT AGA AGC TCT GTG TGT GCA GTT GGG TGA GCT CAT TTT TCC ATT GTG
 N   P   S   R   S   S   V   C   A   V   G   *
       873            882            891            900            909            918
TTG ATA GTT TTG GCT GCC CTT CAC CTC TGG GTG TGT CTG AGA ACT TCT AAG AAC
       927            936            945            954            963            972
TTG TTT TAT CAG TGA CCA TCT CTG TAG TTC AGT TAA CAC TTT CCT CCG AAC TTG
       981            990            999           1008           1017           1026
CTT CAT CTT TAA GTG TTC CTC CCA ACC GCA GGC ATG TAC TTG GGT TCA AAA GAA
      1035           1044           1053           1062           1071           1080
TTC AAC TTT GGG ACC ACA CAC TTT GCA TTC AAA CTG GAA GTC TCA TTC TCT GGA
```

FIGURE 3C

```
     1089            1098            1107            1116            1125            1134
ATT AGA CTG TTT CAT TGA AAA AGA ATG GTG TCC GGC CAG GCG CGG TGG CTC ATG 1143            1152            1161            1170            1179            1188
CCT GTA ATC CCA GCA CTT TGG GAG GCC GAG GCG GGT GGA TCA CCT GAG GTC AGG 1197            1206            1215            1224            1233            1242
AGT TCG AGA CCA GCC TGG CCA ACA TGG TGA AAC CCC TGT CTC TAC TAA AAA TAC 1251            1260            1269            1278            1287            1296
AAA AAA ATT AGC TGG GCG CGG TGG CGC ATG CCT GTA ATC CCA GCT ACT CAG GAG 1305            1314            1323            1332            1341            1350
GCT GAG GCA GGA GAA TCA CTT GAA CCC GGG AGG CAG AGG TTG CAG TGA GCC GAG 1359            1368            1377            1386            1395            1404
ATC ATG CCA TTG CAC TCC AGC CTG GGT GAC AGA GCG AGA CTC CAT CTC AAA AAA 1413            1422            1431            1440            1449            1458
AAT AAA TAA ATA AAT TAT GAA TGA GTA TTT TCT AGA AAT TCA ACT TGC TAA GCC
```

FIGURE 3D

```
          1467      1476      1485      1494      1503      1512
          TGT AAT ACT TAA GGG TAG TTT ATC TAG ATA CAG TAC TTT CTT CCC TGA TAA GTA 1521      1530      1539      1548      1557      1566
          GTA TCA TTG GAG CCC TTA GGT ATA GGA GAA GAG GAA GTT TAA AAA GTG TAA 1575      1584      1593      1602      1611      1620
          GTG GGC CGG GCG TGG CTC ATG CCT GTA ATC CCA GCA CTT TGG GAG GCC GAG 1629      1638      1647      1656      1665      1674
          GCG GGC AGA TCA CAA GGT CAG GAG ATC GAG ACC ATC CTG GCC AAG ATG GTG AAA 1683      1692      1701      1710      1719      1728
          CCC CGT CTC TAC TAA AAA TAC AAA ATT AGC CGG CCG TGG TGG CTC ACA CCT GTA 1737      1746      1755      1764      1773      1782
          ATC CCA GCT ACT TGG GAG GCT GAG GCA GGA GAA TCA CTT GAG GTC AGG AGT TTG 1791      1800      1809      1818      1827      1836
```

FIGURE 3E

```
                AGA CCA GCC TGG CCA ACG TGG TGA AAC CCT GTC TCT ACT AAA AAT ACA AAA ACT
     1845              1854          1863          1872          1881          1890
AGG CCA GGC GCG GGT GGC ACG CCT GTA ATC TCA GCA CTT TGG GAG GCC GAG GCA
     1899              1908          1917          1926          1935          1944
GGT GGA TCA CCT GAG GTC AGG AGT TCA AGA CCA GCC TGG CCA ACA TGG TGA AAC
     1953              1962          1971          1980          1989          1998
CCC ACC TCT ACT AAA AAT ACA AAA ATT AGC CAG GCA TGG TGG TGC ATG CCT GTA
     2007              2016          2025          2034          2043          2052
ATC CCA GCT ACT TGG GAG GCT GAG GCA GGA GAA TTG CTT GAA CCC GGG AGG CAG
     2061              2070          2079          2088          2097          2106
AGG TTG CAG TGA GCC GAG ATC ATG CCA CTG CAC TCC AGC CTG GGT GAC AGA GCG
     2115              2124          2133          2142          2151          2160
AGA CTC CAT TTC AAA AAA AAG AAC TAC AAG TTC TGA TTC CGG ACT CCC AGA TGT
```

FIGURE 3F

```
     2169            2178            2187            2196            2205            2214
GAG TTT TAA TCT CCT CTC CAC TGA TTG ATC CTG ACT AAT CAC TAG CCC CCT GTG 2223            2232            2241            2250            2259            2268
CCC AAT TTC AAC AGT ATG CTG GAG TCA AAT CTG AAC CCC AAA CTA TGC CCT CTT 2277            2286            2295            2304            2313            2322
AAG GGG GGT CCC TCT GGG ATG CCA ACA TGC ATT CAC TTC TTC ACC TGG CTA GGC 2331            2340            2349            2358            2367            2376
ATT CCA TGA GTA TTC ACA TTG TAG TCA CTC CCC TAG GGC TAT GCC CAG GAG TTA 2385            2394            2403            2412            2421            2430
GTA CTT TCC TAC CAC TTG GTG ATC TTG AGT GAG TTT TGG ATG TCC TCA ATG GGT 2439            2448            2457            2466            2475            2484
CCT GAG ATG AGT CAG AGG AGA GCT AGA GTT GGG AAC TGA TCA CCA GTG GCC CCC 2493            2502            2511            2520            2529            2538
CCA GTC CTC AGC TCT TGA AGG AAA GGG AAT GAA TTG CTC TGG CCA TTT GCA TCT
```

FIGURE 3G

```
      2547         2556         2565         2574         2583         2592
GTG CGA AGG ATC GAA CAA AGC CAC TTT CTA CAA TGC AAC CCT GTC CGA CGG CCC 2601         2610         2619         2628         2637         2646
CCT TCC CAA AGC TGC CTG CAA CTT TCA ACC CCG NTG AAT GGA CTT TGG AAC TTG 2655         2664         2673         2682         2691         2700
GGA CAG AGG CAA AGA CTT AAA TGA GGN GCC AAA GNA ATG TCG GGT CCA TTA CCA

2709
AAT TAG GAG GGT NG 3'
```

RAB PROTEINS

This application is a divisional application of U.S. application Ser. No. 08/916,901, filed Aug. 21, 1997 now U.S. Pat. No. 5,892,012.

FIELD OF THE INVENTION

This invention relates to nucleic acid and amino acid sequences of three new human Rab proteins and to the use of these sequences in the diagnosis, prevention, and treatment of inflammation and disorders associated with cell proliferation and apoptosis.

BACKGROUND OF THE INVENTION

Vesicle trafficking is defined as the vesicular transport of materials between different subcellular compartments of eukaryotic cells. Vesicles bud from a donor membrane and fuse with a recipient one carrying internalized materials from one site to another. Rab proteins, low molecular weight (LMW) guanidine triphosphatases (GTPases), belong to the Ras superfamily; they help regulate vesicular transport by directing the vesicles to and from the correct membrane surfaces (Novick, P. and Brennwald, P. (1993) Cell 75: 597–601).

Rab proteins assist the binding of a transport vesicle to its proper acceptor membrane and initiate the membrane fusion process using the energy derived from the hydrolysis of GTP. Rab proteins have a highly variable amino terminus and a prenylated carboxy terminus. The amino terminus contains signal sequences, and the carboxy terminus determines the target membrane to which the Rab protein binds. The targeting process is assisted by a series of escort proteins (Khosravi-Far, R. et al. (1991) Proc. Natl. Acad. Sci. 88: 6264–6268).

In the medial Golgi, it has been shown that GTP-bound Rab proteins initiate the binding of VA-MP-like proteins of the transport vesicle to syntaxin-like proteins on the acceptor membrane triggering membrane fusion events. After transport, GTPase-activating proteins in the target membrane convert the Rab proteins to their GDP-bound state, and guanine-nucleotide dissociation inhibitor helps return the GDP-bound proteins to their membrane of origin.

To date, more than 30 Rab proteins have been identified, and each may have a characteristic intracellular location where it functions in distinct, tissue-specific transport events. For example, Rab2 is important in ER-to-Golgi transport; Rab1 and Rab6 are localized to the Golgi apparatus; Rab3 transports secretory vesicles to the extracellular membrane; Rab5 and Rab7 are localized to the early and late endosomal fusion events, respectively; and Rab 10 mediates vesicle fusion from the medial Golgi to the trans Golgi.

Structurally, the Rab proteins display features characteristic of LMW GTP-binding proteins. Four sequence regions, motifs I–IV, are conserved in the Rab proteins. Motif I, the most variable region among the four, has a signature of GXXXXGK, and the terminal lysine residue interacts with the β- and γ-phosphates of GTP. Motifs II, III, and IV are highly conserved and function in regulating the binding of γ-phosphate, GTP, and the guanine base of GTP, respectively.

In addition to the conserved motifs, the arginine residue following the second GTP-binding domain, the phenylalanine residue adjacent to the fourth GTP-binding domain, and the carboxy terminal cysteines are highly conserved. The cysteines are particularly important in that they are essential for membrane localization. The Rab proteins also have an effector region located in between Motif I and Motif II which has been characterized as the interaction site for GAP, a regulatory protein which stimulates the intrinsic GTPase activity.

Experimental evidence has established the essential role of Rab in vesicle trafficking, cell function, and cell differentiation. Human Rab1, Rab2, Rab3B, Rab4, Rab5, and Rab6 genes isolated from a human pheochromocytoma cDNA library exhibit GTPase activities when produced in E. Coli (Zahraoui, A. et al. (1989) 264: 12394–12401). Although differentially expressed, two isoforms of Rab28, hRab28S and hRab28L, exhibit comparable GTPase-related activities in rat tissues (Brauers, A. et al. (1996) Eur. J. Biochem. 237: 833–840). Localization of murine Rab24 in endoplasmic reticulum/cis-Golgi region of Semliki Forest virus and the vaccinia T7 vector systems indicates that Rab24 may be involved in autophagy-related processes (Olkkonen, V. M. et al. (1993) J. Cell. Sci. 106: 1249–1261). Over expression of Rab proteins significantly enhances the function of Rev, a viral gene essential for processing HIV-1 (Fridell, R.A. et al. (1996) Proc. Natl. Acad. Sci. 93: 4421–4424). A deficiency in the prenylation of one particular Rab is associated with choroideremia, a form of retinal degeneration that causes blindness (Seabra, M. et al. (1996) J. Biol. Chem. 270:24420–24427). Interaction between Rab protein and Cdc2 protein kinase in vitro inhibited vesicle fusion and implicated Rab protein function in mediating cell cycle events (Toumikoski, T. et al. (1989, Nature 342: 942–945). Thus, Rab proteins appear to be involved in the complex and critical processes of vesicle trafficking for the directed release of various molecules.

The discovery of three new human Rab proteins and the polynucleotides encoding them satisfies a need in the art by providing new compositions which are useful in the diagnosis, prevention and treatment of inflammation and disorders associated with cell proliferation and apoptosis.

SUMMARY OF THE INVENTION

The invention features three substantially purified polypeptides, designated individually as RABP-1, RABP-2 and RABP-3 and collectively as RABP having the amino acid sequences shown in SEQ ID NO:1, SEQ ID NO:3, and SEQ ID NO:5.

The invention further provides an isolated and substantially purified polynucleotide sequence encoding the polypeptide RAPB-1, comprising the amino acid sequence of SEQ ID NO: 1 or fragments thereof and compositions comprising said polynucleotide sequence. The invention also provides a polynucleotide sequence which hybridizes under stringent conditions to the polynucleotide sequence encoding the amino acid sequence SEQ ID NO:1 or fragments of said polynucleotide sequence. The invention further provides a polynucleotide sequence comprising the complement of the polynucleotide sequence encoding the amino acid sequence of SEQ ID NO:1, or fragments or variants of said polynucleotide sequence.

The invention also provides an isolated and purified sequence comprising SEQ ID NO:2, or variants thereof. In addition, the invention provides a polynucleotide sequence which hybridizes under stringent conditions to the polynucleotide sequence of SEQ ID NO:2. The invention also provides a polynucleotide sequence comprising the complement of SEQ ID NO:2, or fragments or variants thereof.

The present invention further provides an expression vector containing at least a fragment of any of the claimed polynucleotide sequences. In yet another aspect, the expression vector containing the polynucleotide sequence is contained within a host cell.

The invention also provides a method for producing a polypeptide comprising the amino acid sequence of SEQ ID NO:1, or a fragment thereof, the method comprising the steps of: a) culturing the host cell containing an expression vector containing at least a fragment of the polynucleotide sequence encoding RABP-1 under conditions suitable for the expression of the polypeptide; and b) recovering the polypeptide from the host cell culture.

The invention also provides a pharmaceutical composition comprising a substantially purified RABP-1 having the amino acid sequence of SEQ ID NO:1 in conjunction with a suitable pharmaceutical carrier.

The invention also provides a purified antagonist of the polypeptide of SEQ ID NO:1. In one aspect the invention provides a purified antibody which binds to a polypeptide comprising the amino acid sequence of SEQ ID NO:1.

Still further, the invention provides a purified agonist of the polypeptide of SEQ ID NO:1.

The invention also provides a method for stimulating cell proliferation comprising administering to a cell an effective amount of a pharmaceutical composition comprising purified RABP-1.

The invention also provides a method for treating a disorder associated with an increase in apoptosis comprising administering to a subject in need of such treatment an effective amount of a pharmaceutical composition comprising purified RABP-1.

The invention also provides a method for treating cancer comprising administering to a subject in need of such treatment an effective amount of an antagonist of RABP-1.

The invention also provides a method for treating inflammation comprising administering to a subject in need of such treatment an effective amount of an antagonist of RABP-1.

The invention also provides a method for detecting a polynucleotide which encodes RABP-1 in a biological sample comprising the steps of: a) hybridizing the complement of the polynucleotide sequence which encodes SEQ ID NO:1 to nucleic acid material of a biological sample, thereby forming a hybridization complex; and b) detecting the hybridization complex, wherein the presence of the complex correlates with the presence of a polynucleotide encoding RABP-1 in the biological sample. In one aspect the nucleic acid material of the biological sample is amplified by the polymerase chain reaction prior to hybridization.

Still further, the invention provides an isolated and substantially purified polynucleotide sequence encoding the polypeptide RABP-2, comprising the amino acid sequence of SEQ ID NO:3 or fragments thereof and compositions comprising said polynucleotide sequence. The invention also provides a polynucleotide sequence which hybridizes under stringent conditions to the polynucleotide sequence encoding the amino acid sequence SEQ ID NO:3 or fragments of said polynucleotide sequence. The invention further provides a polynucleotide sequence comprising the complement of the polynucleotide sequence encoding the amino acid sequence of SEQ ID NO:3, or fragments or variants of said polynucleotide sequence.

The invention also provides an isolated and purified sequence comprising SEQ ID NO:4, or variants thereof. In addition, the invention provides a polynucleotide sequence which hybridizes under stringent conditions to the polynucleotide sequence of SEQ ID NO:4. The invention also provides a polynucleotide sequence comprising the complement of SEQ ID NO:4, or fragments or variants thereof.

The present invention further provides an expression vector containing at least a fragment of any of the claimed polynucleotide sequences. In yet another aspect, the expression vector containing the polynucleotide sequence is contained within a host cell.

The invention also provides a method for producing a polypeptide comprising the amino acid sequence of SEQ ID NO:3, or a fragment thereof, the method comprising the steps of: a) culturing the host cell containing an expression vector containing at least a fragment of the polynucleotide sequence encoding RABP-2 under conditions suitable for the expression of the polypeptide; and b) recovering the polypeptide from the host cell culture.

The invention also provides a pharmaceutical composition comprising a substantially purified RABP-2 having the amino acid sequence of SEQ ID NO:3 in conjunction with a suitable pharmaceutical carrier.

The invention also provides a purified antagonist of the polypeptide of SEQ ID NO:3. In one aspect the invention provides a purified antibody which binds to a polypeptide comprising the amino acid sequence of SEQ ID NO:3.

Still further, the invention provides a purified agonist of the polypeptide of SEQ ID NO:3.

The invention also provides a method for stimulating cell proliferation comprising administering to a cell an effective amount of a pharmaceutical composition comprising purified RABP-2.

The invention also provides a method for treating a disorder associated with an increase in apoptosis comprising administering to a subject in need of such treatment an effective amount of a pharmaceutical composition comprising purified RABP-2.

The invention also provides a method for treating cancer comprising administering to a subject in need of such treatment an effective amount of an antagonist of RABP-2.

The invention also provides a method for treating inflammation comprising administering to a subject in need of such treatment an effective amount of an antagonist of RABP-2.

The invention also provides a method for detecting a polynucleotide which encodes RABP-3 (SEQ ID NO:3) in a biological sample comprising the steps of: a) hybridizing the complement of the polynucleotide sequence which encodes SEQ ID NO:3 to nucleic acid material of a biological sample, thereby forming a hybridization complex; and b) detecting the hybridization complex, wherein the presence of the complex correlates with the presence of a polynucleotide encoding RABP-2 in the biological sample. In one aspect the nucleic acid material of the biological sample is amplified by the polymerase chain reaction prior to hybridization.

Still further, the invention provides an isolated and substantially purified polynucleotide sequence encoding the polypeptide RAPB-3, comprising the amino acid sequence of SEQ ID NO:5 or fragments thereof and compositions comprising said polynucleotide sequence; The invention also provides a polynucleotide sequence which hybridizes under stringent conditions to the polynucleotide sequence encoding the amino acid sequence SEQ ID NO:5 or fragments of said polynucleotide sequence. The invention further provides a polynucleotide sequence comprising the complement of the polynucleotide sequence encoding the amino acid sequence of SEQ ID NO:5, or fragments or variants of said polynucleotide sequence.

The invention also provides an isolated and purified sequence comprising SEQ ID NO:6, or variants thereof. In addition, the invention provides a polynucleotide sequence which hybridizes under stringent conditions to the polynucleotide sequence of SEQ ID NO:6. The invention also provides a polynucleotide sequence comprising the complement of SEQ ID NO:6, or fragments or variants thereof.

The present invention further provides an expression vector containing at least a fragment of any of the claimed polynucleotide sequences. In yet another aspect, the expression vector containing the polynucleotide sequence is contained within a host cell.

The invention also provides a method for producing a polypeptide comprising the amino acid sequence of SEQ ID NO:5, or a fragment thereof, the method comprising the steps of: a) culturing the host cell containing an expression vector containing at least a fragment of the polynucleotide sequence encoding RABP-3 under conditions suitable for the expression of the polypeptide; and b) recovering the polypeptide from the host cell culture.

The invention also provides a pharmaceutical composition comprising a substantially purified RABP-3 having the amino acid sequence of SEQ ID NO:5 in conjunction with a suitable pharmaceutical carrier.

The invention also provides a purified antagonist of the polypeptide of SEQ ID NO:5. In one aspect the invention provides a purified antibody which binds to a polypeptide comprising the amino acid sequence of SEQ ID NO:5.

Still further, the invention provides a purified agonist of the polypeptide of SEQ ID NO:5.

The invention also provides a method for stimulating cell proliferation comprising administering to a cell an effective amount of a pharmaceutical composition comprising purified RABP-3.

The invention also provides a method for treating a disorder associated with an increase in apoptosis comprising administering to a subject in need of such treatment an effective amount of a pharmaceutical composition comprising purified RABP-3.

The invention also provides a method for treating cancer comprising administering to a subject in need of such treatment an effective amount of an antagonist of RABP-3.

The invention also provides a method for treating inflammation comprising administering to a subject in need of such treatment an effective amount of an antagonist of RABP-3.

The invention also provides a method for detecting a polynucleotide which encodes RABP-3 in a biological sample comprising the steps of: a) hybridizing the complement of the polynucleotide sequence which encodes SEQ ID NO:5 to nucleic acid material of a biological sample, thereby forming a hybridization complex; and b) detecting the hybridization complex, wherein the presence of the complex correlates with the presence of a polynucleotide encoding RABP-3 in the biological sample. In one aspect the nucleic acid material of the biological sample is amplified by the polymerase chain reaction prior to hybridization.

BRIEF DESCRIPTION OF THE FIGURES

FIGS. 1A, 1B, 1C, and 1D show the amino acid sequence (SEQ ID NO: 1) and nucleic acid sequence (SEQ ID NO:2) of RABP-1. The alignment was produced using MACDNASIS PRO software (Hitachi Software Engineering Co. Ltd. San Bruno, Calif.).

FIGS. 2A, 2B, and 2C show the amino acid sequence (SEQ ID NO:3) and nucleic acid sequence (SEQ ID NO:4) of RABP-2. The alignment was produced using MACDNASIS PRO software (Hitachi Software Engineering Co. Ltd. San Bruno, Calif).

FIGS. 3A, 3B, 3C, 3D, 3E, 3F, 3G, and 3H show the amino acid sequence (SEQ ID NO:5) and nucleic acid sequence (SEQ ID NO:6) of RABP-3. The alignment was produced using MACDNASIS PRO software (Hitachi Software Engineering Co. Ltd. San Bruno, Calif).

FIG. 4 shows the amino acid sequence alignments between RABP-1 (2312652; SEQ ID NO:1) and a mouse Rab24 (GI 438164; SEQ ID NO:7), produced using the multisequence alignment program of DNASTAR software (DNASTAR Inc, Madison Wis.).

FIG. 5 shows the amino acid sequence alignments between RABP-2 (2514506; SEQ ID NO:3) and a rat Rab1B (GI 57006; SEQ ID NO:8), produced using the multisequence alignment program of DNASTAR software (DNASTAR Inc, Madison WI).

FIG. 6 shows the amino acid sequence alignments between RABP-3 (3400003; SEQ ID NO:5) and a rat Rab28 (GI 1154901; SEQ ID NO:9), produced using the multisequence alignment program of DNASTART software (DNASTAR Inc, Madison Wis.).

DESCRIPTION OF THE INVENTION

Figure 7A:
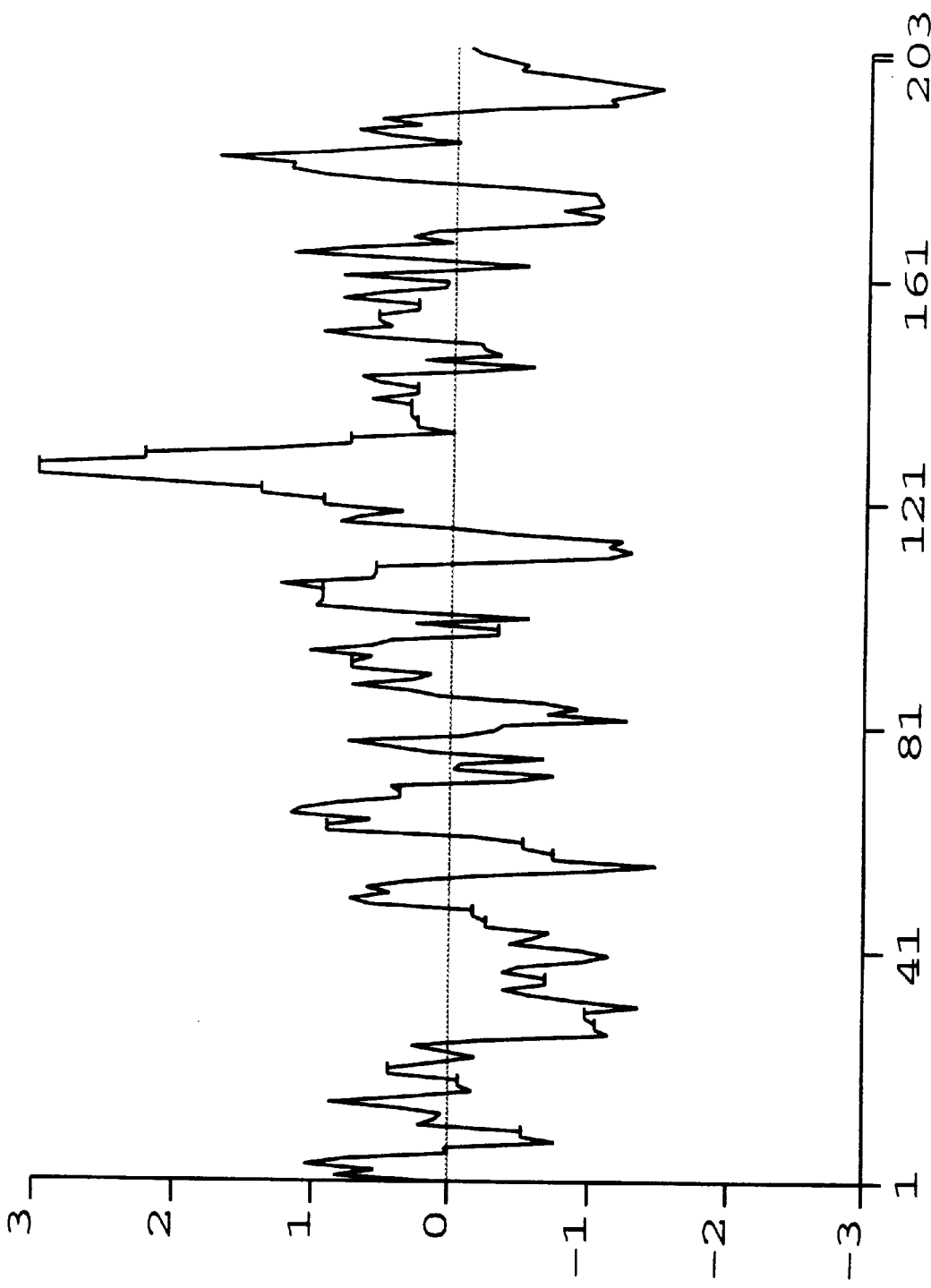
FIGS. 7A and 7B show the hydrophobicity plots for RABP-1 (SEQ ID NO:1) and mouse Rab24 (SEQ ID NO:7), respectively. The positive X axis reflects amino acid position, and the negative Y axis, hydrophobicity (MACDNASIS PRO software).

Before the present proteins, nucleotide sequences, and methods are described, it is understood that this invention is not limited to the particular methodology, protocols, cell lines, vectors, and reagents described, as these may vary. It is also to be understood that the terminology used herein is for the purpose of describing particular embodiments only, and is not intended to limit the scope of the present invention which will be limited only by the appended claims.

It must be noted that as used herein and in the appended claims, the singular forms "a", "an", and "the" include plural reference unless the context clearly dictates otherwise. Thus, for example, reference to "a host cell" includes a plurality of such host cells, reference to the "antibody" is a reference to one or more antibodies and equivalents thereof known to those skilled in the art, and so forth.

Unless defined otherwise, all technical and scientific terms used herein have the same meanings as commonly understood by one of ordinary skill in the art to which this invention belongs. Although any methods and materials similar or equivalent to those described herein can be used in the practice or testing of the present invention, the preferred methods, devices, and materials are now described. All publications mentioned herein are incorporated herein by reference for the purpose of describing and disclosing the cell lines, vectors, and methodologies which are reported in the publications which might be used in connection with the invention. Nothing herein is to be construed as an admission that the invention is not entitled to antedate such disclosure by virtue of prior invention.

DEFINITIONS

RABP, as used herein, refers to the amino acid sequences of substantially purified RABP obtained from any species, particularly mammalian, including bovine, ovine, porcine, murine, equine, and preferably human, from any source whether natural, synthetic, semi-synthetic, or recombinant.

The term "agonist", as used herein, refers to a molecule which, when bound to RABP, increases or prolongs the duration of the effect of RABP. Agonists may include proteins, nucleic acids, carbohydrates, or any other molecules which bind to and modulate the effect of RABP.

An "allele" or "allelic sequence", as used herein, is an alternative form of the gene encoding RABP. Alleles may result from at least one mutation in the nucleic acid sequence and may result in altered mRNAs or polypeptides whose structure or function may or may not be altered. Any given natural or recombinant gene may have none, one, or many allelic forms. Common mutational changes which give rise to alleles are generally ascribed to natural deletions, additions, or substitutions of nucleotides. Each of these types of changes may occur alone, or in combination with the others, one or more times in a given sequence.

"Altered" nucleic acid sequences encoding RABP, as used herein, include those with deletions, insertions, or substitutions of different nucleotides resulting in a polynucleotide that encodes the same or a functionally equivalent RABP. Included within this definition are polymorphisms which may or may not be readily detectable using a particular oligonucleotide probe of the polynucleotide encoding RABP, and improper or unexpected hybridization to alleles, with a locus other than the normal chromosomal locus for the polynucleotide sequence encoding RABP. The encoded protein may also be "altered" and contain deletions, insertions, or substitutions of amino acid residues which produce a silent change and result in a functionally equivalent RABP. Deliberate amino acid substitutions may be made on the basis of similarity in polarity, charge, solubility, hydrophobicity, hydrophilicity, and/or the amphipathic nature of the residues as long as the biological or immunological activity of RABP is retained. For example, negatively charged amino acids may include aspartic acid and glutamic acid; positively charged amino acids may include lysine and arginine; and amino acids with uncharged polar head groups having similar hydrophilicity values may include leucine, isoleucine, and valine, glycine and alanine, asparagine and glutamine, serine and threonine, and phenylalanine and tyrosine.

"Amino acid sequence", as used herein, refers to an oligopeptide, peptide, polypeptide, or protein sequence, and fragment thereof, and to naturally occurring or synthetic molecules. Fragments of RABP are preferably about 5 to about 15 amino acids in length and retain the biological activity or the immunological activity of RABP. Where "amino acid sequence" is recited herein to refer to an amino acid sequence of a naturally occurring protein molecule, amino acid sequence, and like terms, are not meant to limit the amino acid sequence to the complete, native amino acid sequence associated with the recited protein molecule.

"Amplification", as used herein, refers to the production of additional copies of a nucleic acid sequence and is generally carried out using polymerase chain reaction (PCR) technologies well known in the art (Dieffenbach, C. W. and G. S. Dveksler (1995) *PRC Primer, a Laboratory Manual*, Cold Spring Harbor Press, Plainview, N.Y.).

The term "antagonist", as used herein, refers to a molecule which, when bound to RABP, decreases the amount or the duration of the effect of the biological or immunological activity of RABP. Antagonists may include proteins, nucleic acids, carbohydrates, antibodies or any other molecules which decrease the effect of RABP.

As used herein, the term "antibody" refers to intact molecules as well as fragments thereof, such as Fa, F(ab')$_2$, and Fv, which are capable of binding the epitopic determinant. Antibodies that bind RABP polypeptides can be prepared using intact polypeptides or fragments containing small peptides of interest as the immunizing antigen. The polypeptide or oligopeptide used to immunize an animal can be derived from the translation of RNA or synthesized chemically and can be conjugated to a carrier protein, if desired. Commonly used carriers that are chemically coupled to peptides include bovine serum albumin and thyroglobulin, keyhole limpet hemocyanin. The coupled peptide is then used to immunize the animal (e.g., a mouse, a rat, or a rabbit).

The term "antigenic determinant", as used herein, refers to that fragment of a molecule (i.e., an epitope) that makes contact with a particular antibody. When a protein or fragment of a protein is used to immunize a host animal, numerous regions of the protein may induce the production of antibodies which bind specifically to a given region or three-dimensional structure on the protein; these regions or structures are referred to as antigenic determinants. An antigenic determinant may compete with the intact antigen (i.e., the immunogen used to elicit the immune response) for binding to an antibody.

The term "antisense", as used herein, refers to any composition containing nucleotide sequences which are complementary to a specific DNA or RNA sequence. The term "antisense strand" is used in reference to a nucleic acid strand that is complementary to the "sense" strand. Antisense molecules include peptide nucleic acids and may be produced by any method including synthesis or transcription. Once introduced into a cell, the complementary nucleotides combine with natural sequences produced by the cell to form duplexes and block either transcription or translation. The designation "negative" is sometimes used in reference to the antisense strand, and "positive" is sometimes used in reference to the sense strand.

The term "biologically active", as used herein, refers to a protein having structural, regulatory, or biochemical functions of a naturally occurring molecule. Likewise, "immunologically active" refers to the capability of the natural, recombinant, or synthetic RABP, or any oligopeptide thereof, to induce a specific immune response in appropriate animals or cells and to bind with specific antibodies.

The terms "complementary" or "complementary", as used herein, refer to the natural binding of polynucleotides under permissive salt and temperature conditions by base-pairing. For example, the sequence "A-G-T" binds to the complementary sequence "T-C-A". Complementarity between two single-stranded molecules may be "partial", in which only some of the nucleic acids bind, or it may be complete when total complementary exists between the single stranded molecules. The degree of complementary between nucleic acid strands has significant effects on the efficiency and strength of hybridization between nucleic acid strands. This is of particular importance in amplification reactions, which depend upon binding between nucleic acids strands and in the design and use of PNA molecules.

A "composition comprising a given polynucleotide sequence", as used herein, refers broadly to any composition containing the given polynucleotide sequence. The composition may comprise a dry formulation or an aqueous solution. Compositions comprising polynucleotide sequences encoding RABP (SEQ ID NO:1, SEQ ID NO:3, or SEQ ID NO:5) or fragments thereof (e.g., SEQ ID NO:2, SEQ ID NO:4, SEQ ID NO:6 and fragments thereof) may be employed as hybridization probes. The probes may be stored in freeze-dried form and may be associated with a stabilizing agent such as a carbohydrate. In hybridizations, the probe may be deployed in an aqueous solution containing salts (e.g., NaCl), detergents (e.g., SDS) and other components (e.g., Denhardt's solution, dry milk, salmon sperm DNA, etc.). "Consensus", as used herein, refers to a nucleic acid sequence which has been resequenced to resolve uncalled bases, has been extended using XL-PCR (Perkin Elmer, Norwalk, Conn.) in the 5' and/or the 3' direction and resequenced, or has been assembled from the overlapping sequences of more than one Incyte Clone using a computer program for fragment assembly (e.g., GELVIEW Fragment Assembly system, GCG, Madison, Wis.). Some sequences have been both extended and assembled to produce the consensus sequence.

The term "correlates with expression of a polynucleotide", as used herein, indicates that the detection of the presence of ribonucleic acid that is similar to SEQ ID NO:2, SEQ ID NO:4, or SEQ ID NO:6 by northern analysis is indicative of the presence of mRNA encoding RABP in a sample and thereby correlates with expression of the transcript from the polynucleotide encoding the protein.

A "deletion", as used herein, refers to a change in the amino acid or nucleotide sequence and results in the absence of one or more amino acid residues or nucleotides.

The term "derivative", as used herein, refers to the chemical modification of a nucleic acid encoding or complementary to RABP or the encoded RABP. Such modifications include, for example, replacement of hydrogen by an alkyl, acyl, or amino group. A nucleic acid derivative encodes a polypeptide which retains the biological or immunological function of the natural molecule. A derivative polypeptide is one which is modified by glycosylation, pegylation, or any similar process which retains the biological or immunological function of the polypeptide from which it was derived.

The term "homology", as used herein, refers to a degree of complementarity. There may be partial homology or complete homology (i.e., identity). A partially complementary sequence that at least partially inhibits an identical sequence from hybridizing to a target nucleic acid is referred to using the functional term "substantially homologous." The inhibition of hybridization of the completely complementary sequence to the target sequence may be examined using a hybridization assay (Southern or northern blot, solution hybridization and the like) under conditions of low stringency. A substantially homologous sequence or hybridization probe will compete for and inhibit the binding of a completely homologous sequence to the target sequence under conditions of low stringency. This is not to say that conditions of low stringency are such that non-specific binding is permitted; low stringency conditions require that the binding of two sequences to one another be a specific (i.e., selective) interaction. The absence of non-specific binding may be tested by the use of a second target sequence which lacks even a partial degree of complementarity (e.g., less than about 30% identity). In the absence of non-specific binding, the probe will not hybridize to the second non-complementary target sequence.

Human artificial chromosomes (HACs) are linear microchromosomes which may contain DNA sequences of 10K to 10M in size and contain all of the elements required for stable mitotic chromosome segregation and maintenance (Harrington, J. J. et al. (1997) Nat Genet. 15:345–355).

The term "humanized antibody", as used herein, refers to antibody molecules in which amino acids have been replaced in the non-antigen binding regions in order to more closely resemble a human antibody, while still retaining the original binding ability.

The term "hybridization", as used herein, refers to any process by which a strand of nucleic acid binds with a complementary strand through base pairing.

The term "hybridization complex", as used herein, refers to a complex formed between two nucleic acid sequences by virtue of the formation of hydrogen bonds between complementary G and C bases and between complementary A and T bases; these hydrogen bonds may be further stabilized by base stacking interactions. The two complementary nucleic acid sequences hydrogen bond in an antiparallel configuration. A hybridization complex may be formed in solution (e.g., $C_0t$ or $R_0t$ analysis) or between one nucleic acid sequence present in solution and another nucleic acid sequence immobilized on a solid support (e.g., paper, membranes, filters, chips, pins or glass slides, or any other appropriate substrate to which cells or their nucleic acids have been fixed).

An "insertion" or "addition", as used herein, refers to a change in an amino acid or nucleotide sequence resulting in the addition of one or more amino acid residues or nucleotides, respectively, as compared to the naturally occurring molecule.

"Microarray" refers to an array of distinct polynucleotides or oligonucleotides synthesized on a substrate, such as paper, nylon or other type of membrane, filter, chip, glass slide, or any other suitable solid support.

The term "modulate", as used herein, refer to a change in the activity of RABP. For example, modulation may cause an increase or a decrease in protein activity, binding characteristics, or any other biological, functional or immunological properties of RABP. "Nucleic acid sequence", as used herein, refers to an oligonucleotide, nucleotide, or polynucleotide, and fragments thereof, and to DNA or RNA of genomic or synthetic origin which may be single- or double-stranded, and represent the sense or antisense strand. "Fragments" are those nucleic acid sequences which are greater than 60 nucleotides than in length, and most preferably includes fragments that are at least 100 nucleotides or at least 1000 nucleotides, and at least 10,000 nucleotides in length.

The term "oligonucleotide" refers to a nucleic acid sequence of at least about 6 nucleotides to about 60 nucleotides, preferably about 15 to 30 nucleotides, and more preferably about 20 to 25 nucleotides, which can be used in PCR amplification or a hybridization assay, or a microarray. As used herein, oligonucleotide is substantially equivalent to the terms "amplimers","primers", "oligomers", and "probes", as commonly defined in the art.

"Peptide nucleic acid", PNA, as used herein, refers to an antisense molecule or anti-gene agent which comprises an oligonucleotide of at least five nucleotides in length linked to a peptide backbone of amino acid residues which ends in lysine. The terminal lysine confers solubility to the composition. PNAs may be pegylated to extend their lifespan in the cell where they preferentially bind complementary single stranded DNA and RNA and stop transcript elongation (Nielsen, P. E. et al. (1993) Anticancer Drug Des. 8:53–63).

The term "portion", as used herein, with regard to a protein (as in "a portion of a given protein") refers to fragments of that protein. The fragments may range in size from five amino acid residues to the entire amino acid sequence minus one amino acid. Thus, a protein "comprising at least a portion of the amino acid sequence of SEQ ID NO:1, SEQ ID NO:3, or SEQ ID NO:5" encompasses the full-length RABP and fragments thereof.

The term "sample", as used herein, is used in its broadest sense. A biological sample suspected of containing nucleic acid encoding RABP, or fragments thereof, or RABP itself may comprise a bodily fluid, extract from a cell, chromosome, organelle, or membrane isolated from a cell, a cell, genomic DNA, RNA, or cDNA (in solution or bound to a solid support), a tissue, a tissue print, and the like.

The terms "specific binding" or "specifically binding", as used herein, refer to that interaction between a protein or peptide and an agonist, an antibody and an antagonist. The interaction is dependent upon the presence of a particular structure (i.e., the antigenic determinant or epitope) of the protein recognized by the binding molecule. For example, if an antibody is specific for epitope "A", the presence of a protein containing epitope A (or free, unlabeled A) in a reaction containing labeled "A" and the antibody will reduce the amount of labeled A bound to the antibody.

The terms "stringent conditions" or "stringency", as used herein, refer to the conditions for hybridization as defined by the nucleic acid, salt, and temperature. These conditions are well known in the art and may be altered in order to identify or detect identical or related polynucleotide sequences. Numerous equivalent conditions comprising either low or high stringency depend on factors such as the length and nature of the sequence (DNA, RNA, base composition), nature of the target (DNA, RNA, base composition), milieu (in solution or immobilized on a solid substrate), concentration of salts and other components (e.g., formamide, dextran sulfate and/or polyethylene glycol), and temperature of the reactions (within a range from about 5° C. below the melting temperature of the probe to about 20° C. to 25° C. below the melting temperature). One or more factors be may be varied to generate conditions of either low or high stringency different from, but equivalent to, the above listed conditions.

The term "substantially purified", as used herein, refers to nucleic or amino acid sequences that are removed from their natural environment, isolated or separated, and are at least 60% free, preferably 75% free, and most preferably 90% free from other components with which they are naturally associated.

A "substitution", as used herein, refers to the replacement of one or more amino acids or nucleotides by different amino acids or nucleotides, respectively. "Transformation", as defined herein, describes a process by which exogenous DNA enters and changes a recipient cell. It may occur under natural or artificial conditions using various methods well known in the art. Transformation may rely on any known method for the insertion of foreign nucleic acid sequences into a prokaryotic or eukaryotic host cell. The method is selected based on the type of host cell being transformed and may include, but is not limited to, viral infection, electroporation, heat shock, lipofection, and particle bombardment. Such "transformed" cells include stably transformed cells in which the inserted DNA is capable of replication either as an autonomously replicating plasmid or as part of the host chromosome. They also include cells which transiently express the inserted DNA or RNA for limited periods of time.

A "variant" of RABP, as used herein, refers to an amino acid sequence that is altered by one or more amino acids. The variant may have "conservative" changes, wherein a substituted amino acid has similar structural or chemical properties, e.g., replacement of leucine with isoleucine. More rarely, a variant may have "nonconservative" changes, e.g., replacement of a glycine with a tryptophan. Analogous minor variations may also include amino acid deletions or insertions, or both. Guidance in determining which amino acid residues may be substituted, inserted, or deleted without abolishing biological or immunological activity may be found using computer programs well known in the art, for example, DNASTAR software.

THE INVENTION

The invention is based on the discovery of three new human Rab proteins (hereinafter collectively referred to as "RABP"), the polynucleotides encoding RABP, and the use of these compositions for the diagnosis, prevention, or treatment of inflammation and disorders associated with cell proliferation and apoptosis.

Nucleic acids encoding the RABP-1 of the present invention were first identified in Incyte Clone 2312652 from a tumorous neuroganglion tissue cDNA library (NGANNOT01) using a computer search for amino acid sequence alignments. A consensus sequence, SEQ ID NO:2, was derived from the following overlapping and/or extended nucleic acid sequences: Incyte Clones 2312652 (NGANNOT01), 1851992 (LUNGFET03), 1234510 (LUNGFET03), 1880394 (LEUKNOT03), 2209748 (SINTFET03), 1439042 (PANCNOT08), and 487135 (HNT2AGT01).

Nucleic acids encoding the RABP-2 of the present invention were first identified in Incyte Clone 2514506 from a liver tumor tissue cDNA library (LIVRTUT04) using a computer search for amino acid sequence alignments. A consensus sequence, SEQ ID NO:4, was derived from the following overlapping and/or extended nucleic acid sequences: Incyte Clones 2530505 (GBLANOT02), 1400140 (BRAITUT08), 2619847 (KERANOT02), and 2514506 (LIVRTUT04).

Nucleic acids encoding the RABP-3 of the present invention were first identified in Incyte Clone 3400003 from a nontumorous corpus cavemosum tissue cDNA library (UTRSNOT16) using a computer search for amino acid sequence alignments. A consensus sequence, SEQ ID NO:6, was derived from the following overlapping and/or extended nucleic acid sequences: Incyte Clones 3400003 (UTRSNOT16), 3440023 (PENCNOT06), 1804977 (SINTNOT13), 938735 (CERVNOTO1), 473298 (MMLRIDT01), 882035 (THYRNOT02), and 623472 (PGANNOT01).

Figure 7B:
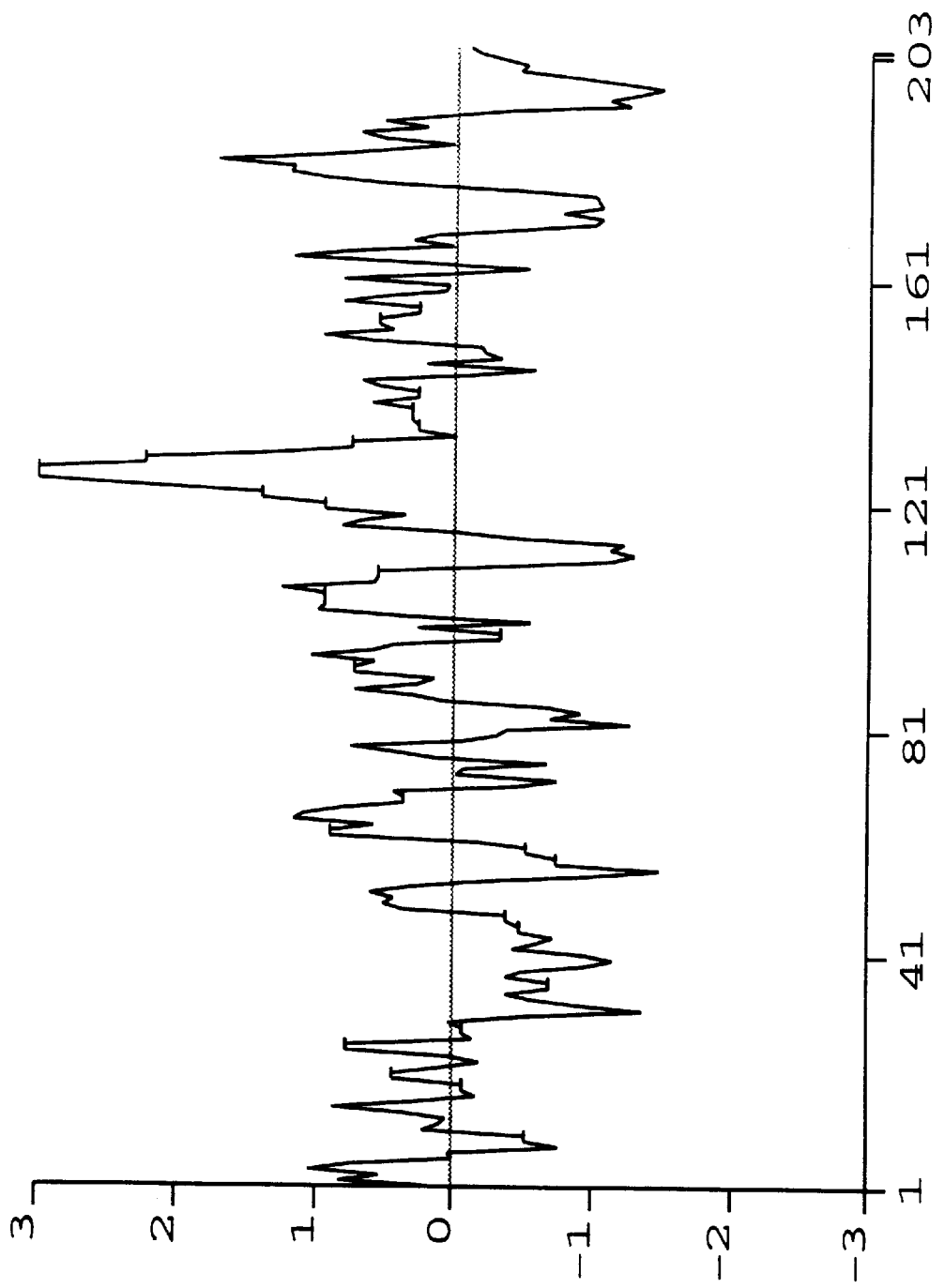

In one embodiment, the invention encompasses a polypeptide, RABP-1, comprising the amino acid sequence of SEQ ID NO: 1, as shown in FIGS. 1A, 1B, 1C, and 1D. RABP-1 is 203 amino acids in length. It has four conserved GTP-binding sites encompassing residues G14-K20, D63-E68, T120-D123, and E152-K156, analogous to other LMW GTP-binding proteins. It also has the conserved arginine, R79, and phenylalanine, F165. The effector site for binding GAP encompasses residues T40-F45. The carboxy terminus of RABP-1 has the two conserved cysteine residues for binding lipid. RABP-1 has six potential casein kinase II phosphorylation sites encompassing residues S22-E25, S51-D54, S94-E97, S108-E111, T120-D123, and S160-E163, and two potential protein kinase C phosphorylation sites encompassing residues S67-R69 and S154-K156. As shown in FIG. 4, RABP-1 has chemical and structural homology with a mouse Rab24 (GI 438164; SEQ ID NO:7). In particular, RABP and the mouse Rab24 share 97% sequence homology. As illustrated by FIGS. 7A and 7B, RABP-1 and the mouse Rab24 have rather similar hydrophobicity plots. Northern analysis shows the expression of RABP-1 in various cDNA libraries, at least 29% of which are immortalized or cancerous, at least 19% of which involve immune response, and at least 26% are expressed in fetal/infant tissues or organs.

Figure 8A:
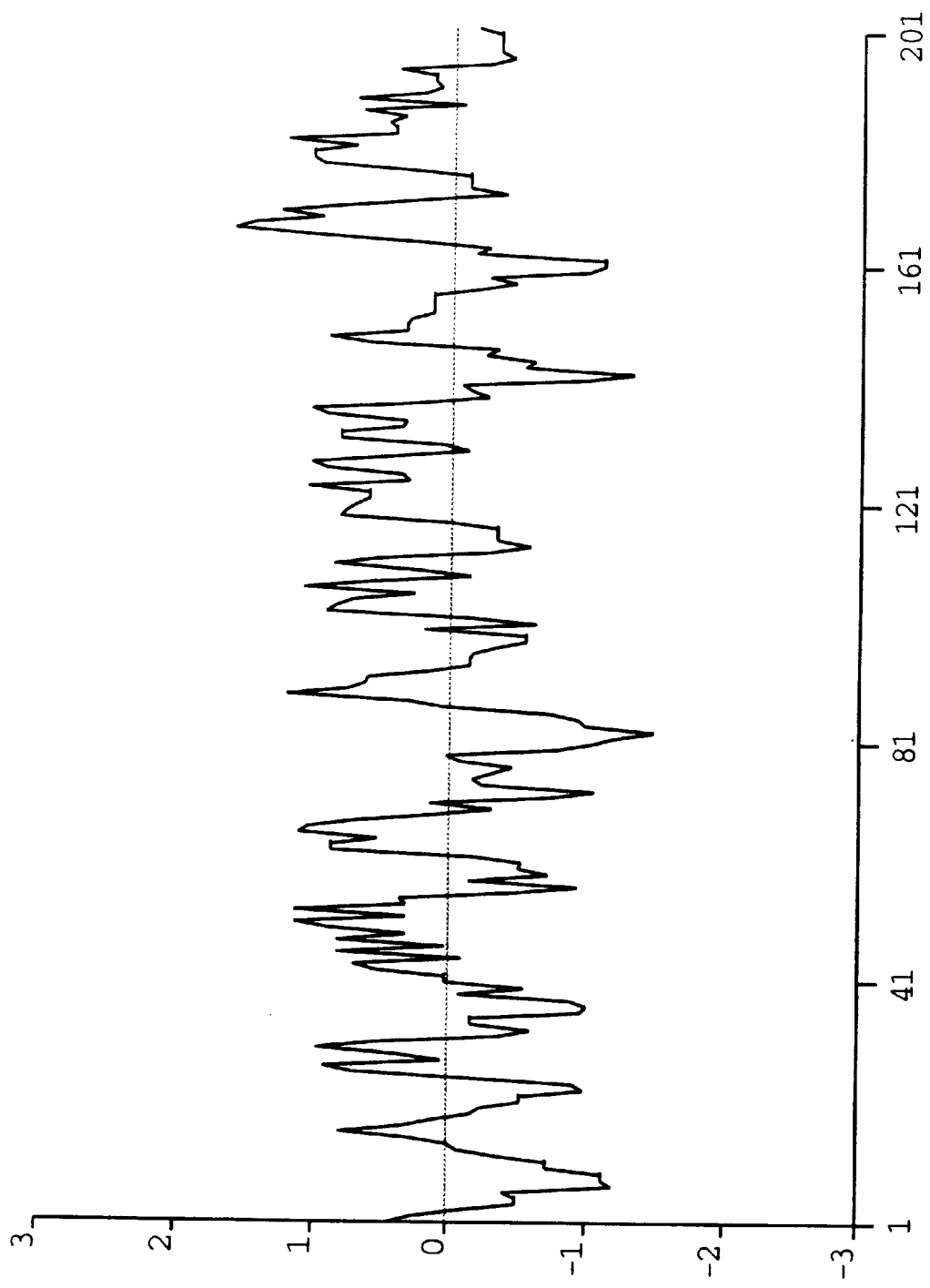
FIGS. 8A and 8B show the hydrophobicity plots for RABP-2 (SEQ ID NO: 3) and the rat Rab1B (SEQ ID NO:8), respectively. The positive X axis reflects amino acid position, and the negative Y axis, hydrophobicity (MACDNASIS PRO software).
Figure 8B:
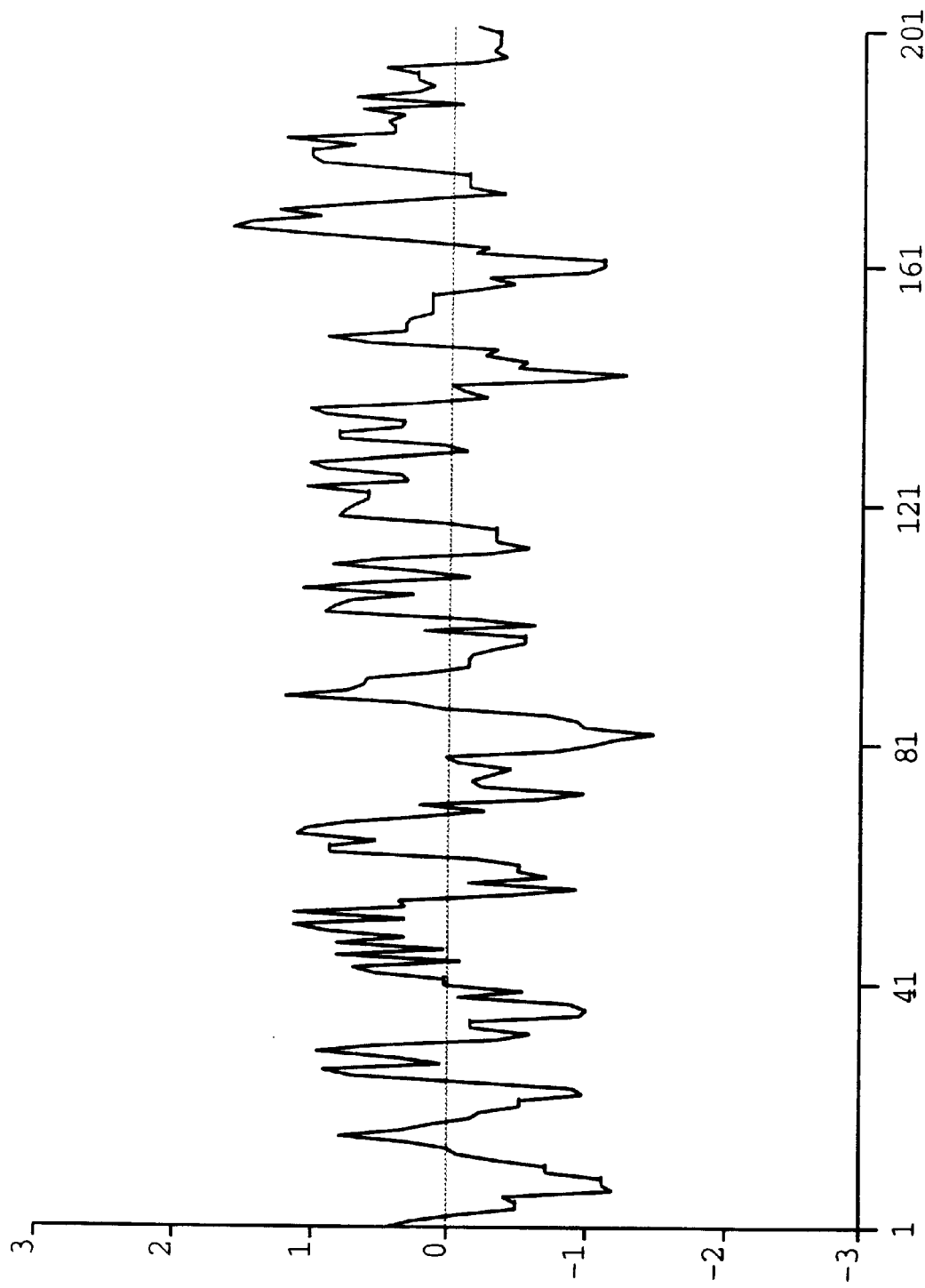

In another embodiment, the invention encompasses a polypeptide, RABP-2, comprising the amino acid sequence of SEQ ID NO:3, as shown in FIGS. 2A, 2B, and 2C. RABP-2 is 201 amino acids in length. It has four conserved GTP-binding sites encompassing residues G15-S22, D63-E68, N121-D124, and E149-K153, analogous to other LMW GTP-binding proteins. It also has the conserved arginine, R79, and phenylalanine, F 162. The effector site for binding GAP encompasses residues T40-F45. The carboxy terminus of RABP-2 has the two conserved cysteine residues for binding lipid. RABP-2 has three potential N-glycosylation sites encompassing residues N121-D124, N133-A136, and N154-N157; five potential casein kinase II phosphorylation sites encompassing residues T32-E35, T91-E94, T135-E138, T156-E159, and S179-E182; one potential tyrosine kinase phosphrylation site encompassing residues R27-Y33; and five potential protein kinase C phosphorylation sites encompassing residues T56-K58, T126-K128, T127-K129, T135-K137, and S151-K153. As shown in FIG. 5, RABP-2 has chemical and structural homology with a rat Rab1 B (GI 57006; SEQ ID NO:8). In particular, RABP and the rat Rab1 B share 98% sequence homology. As illustrated by FIGS. 8A and 8B, RABP-2 and the rat Rab1 B have rather similar hydrophobicity plots. Northern analysis shows the expression of RABP-2 in various cDNA libraries, at least 50% of which are immortalized or cancerous, at least 14% of which involve immune response, and at least 14% are expressed in fetal/infant tissues or organs.

Figure 9A:
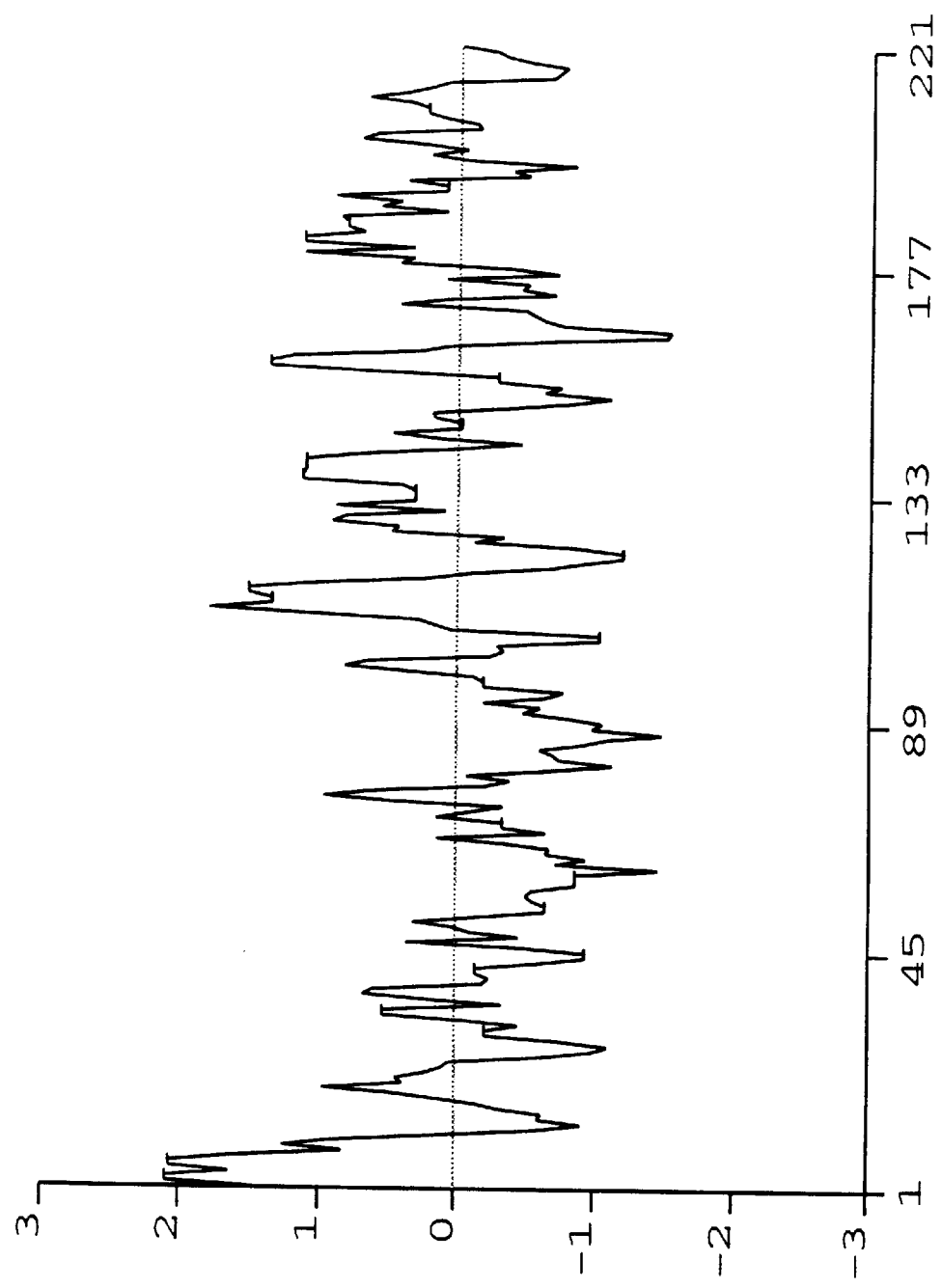
FIGS. 9A and 9B show the hydrophobicity plots for RABP-3 (SEQ ID NO: 5) and the rat Rab28 (SEQ ID NO:9), respectively. The positive X axis reflects amino acid position, and the negative Y axis, hydrophobicity (MACDNASIS PRO software).
Figure 9B:
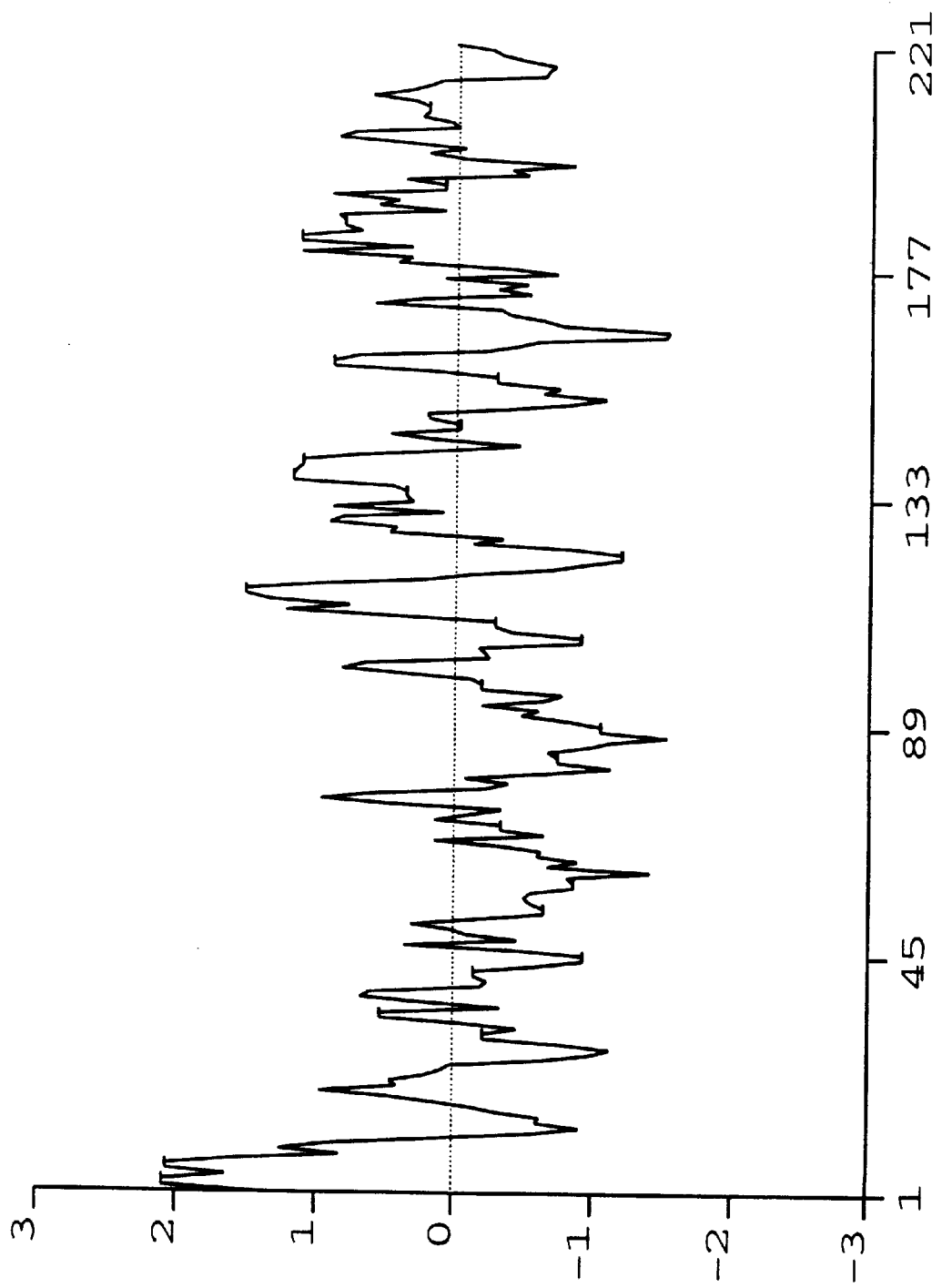

In a further embodiment, the invention encompasses a polypeptide, RABP-3, comprising the amino acid sequence of SEQ ID NO:5, as shown in FIGS. 3A, 3B, 3C, 3D, 3E, 3F, 3G, and 3H. RABP-3 is 221 amino acids in length. It has four conserved GTP-binding sites encompassing residues G19-K25, D68-T73, N129-D132, and F157-K161, analogous to other LMW GTP-binding proteins. The effector site for binding GAP encompasses residues T44-F49. The carboxy terminus of RABP-3 has a conserved CAAX box encompassing residues C218-G221 for binding lipid. RABP-3 has one potential N-glycosylation site encompassing residues N61 -L64; two potential cAMP- and cGMP-dependent protein kinase phosphorylation sites encompassing residues R52-T55 and K112-S115; one potential casein kinase II phosphorylation sites encompassing residues S2-E5 and S4-E7; one potential tyrosine kinase phosphrylation site encompassing residues K77-Y84; and four potential protein kinase C phosphorylation sites encompassing residues S23-K25, T138-K140, S159-K161, and S190-R192. As shown in FIG. 6, RABP-3 has chemical and structural homology with a rat Rab28 (GI 1154901; SEQ ID NO:9). In particular, RABP and the rat Rab28 share 92% sequence homology. As illustrated by FIGS. 9A and 9B, RABP-3 and the rat Rab28 have rather similar hydrophobicity plots. Northern analysis shows the expression of RABP-3 in various cDNA libraries, at least 50% of which are immortalized or cancerous, at least 21% of which involve immune response, and at least 11% are expressed in fetal/infant tissues or organs.

The invention also encompasses RABP variants. A preferred RABP variant is one having at least 80%, and more preferably at least 90%, amino acid sequence identity to the RABP amino acid sequence (SEQ ID NO:1, SEQ ID NO:3, or SEQ ID NO:5 ) and which retains at least one biological, immunological or other functional characteristic or activity of RABP. A most preferred RABP variant is one having at least 95% amino acid sequence identity to SEQ ID NO: 1, SEQ ID NO:3, or SEQ ID NO:5.

The invention also encompasses polynucleotides which encode RABP. Accordingly, any nucleic acid sequence which encodes the amino acid sequence of RABP can be used to produce recombinant molecules which express RABP. In a particular embodiment, the invention encompasses the polynucleotide comprising the nucleic acid sequence of SEQ ID NO:2, SEQ ID NO:4, or SEQ ID NO:6 as shown in FIGS. 1A, 1B, 1C, and 1D, FIGS. 2A, 2B, and 2C, or FIGS. 3A, 3B, 3C, 3D, 3E, 3F, 3G, and 3H.

It will be appreciated by those skilled in the art that as a result of the degeneracy of the genetic code, a multitude of nucleotide sequences encoding RABP, some bearing minimal homology to the nucleotide sequences of any known and naturally occurring gene, may be produced. Thus, the invention contemplates each and every possible variation of nucleotide sequence that could be made by selecting combinations based on possible codon choices. These combinations are made in accordance with the standard triplet genetic code as applied to the nucleotide sequence of naturally occurring RABP, and all such variations are to be considered as being specifically disclosed.

Although nucleotide sequences which encode RABP and its variants are preferably capable of hybridizing to the nucleotide sequence of the naturally occurring RABP under appropriately selected conditions of stringency, it may be advantageous to produce nucleotide sequences encoding RABP or its derivatives possessing a substantially different codon usage. Codons may be selected to increase the rate at which expression of the peptide occurs in a particular prokaryotic or eukaryotic host in accordance with the frequency with which particular codons are utilized by the host. Other reasons for substantially altering the nucleotide sequence encoding RABP and its derivatives without altering the encoded amino acid sequences include the production of RNA transcripts having more desirable properties, such as a greater half-life, than transcripts produced from the naturally occurring sequence.

The invention also encompasses production of DNA sequences, or fragments thereof, which encode RABP and its derivatives, entirely by synthetic chemistry. After production, the synthetic sequence may be inserted into any of the many available expression vectors and cell systems using reagents that are well known in the art. Moreover, synthetic chemistry may be used to introduce mutations into a sequence encoding RABP or any fragment thereof.

Also encompassed by the invention are polynucleotide sequences that are capable of hybridizing to the claimed nucleotide sequences, and in particular, those shown in SEQ ID NO:2, SEQ ID NO:4, or SEQ ID NO:6, under various conditions of stringency as taught in Wahl, G. M. and S. L. Berger (1987; Methods Enzymol. 152:399–407) and Kimmel, A. R. (1987; Methods Enzymol. 152:507–51 1).

Methods for DNA sequencing which are well known and generally available in the art and may be used to practice any of the embodiments of the invention. The methods may employ such enzymes as the Klenow fragment of DNA polymerase I, SEQUENASE (US Biochemical Corp, Cleveland, Ohio.), Taq polymerase (Perkin Elmer), thermostable T7 polymerase (Amersham, Chicago, Ill.), or combinations of polymerases and proofreading exonucleases such as those found in the ELONGASE Amplification System marketed by Gibco/BRL (Gaithersburg, Md.). Preferably, the process is automated with machines such as the Hamilton Micro Lab 2200 (Hamilton, Reno, Nev.), Peltier Thermal Cycler (PTC200; MJ Research, Watertown, Mass.) and the ABI Catalyst and 373 and 377 DNA Sequencers (Perkin Elmer).

The nucleic acid sequences encoding RABP may be extended utilizing a partial nucleotide sequence and employing various methods known in the art to detect upstream sequences such as promoters and regulatory elements. For example, one method which may be employed, "restriction-site" PCR, uses universal primers to retrieve unknown sequence adjacent to a known locus (Sarkar, G. (1993) PCR Methods Applic. 2:318–322). In particular, genomic DNA is first amplified in the presence of primer to a linker sequence and a primer specific to the known region. The amplified sequences are then subjected to a second round of PCR with the same linker primer and another specific primer internal to the first one. Products of each round of PCR are transcribed with an appropriate RNA polymerase and sequenced using reverse transcriptase.

Inverse PCR may also be used to amplify or extend sequences using divergent primers based on a known region (Triglia, T. et al. (1988) Nucleic Acids Res. 16:8186). The primers may be designed using commercially available software such as OLIGO 4.06 Primer Analysis software (National Biosciences Inc., Plymouth, Minn.), or another appropriate program, to be 22–30 nucleotides in length, to have a GC content of 50% or more, and to anneal to the target sequence at temperatures about 68°–72° C. The method uses several restriction enzymes to generate a suitable fragment in the known region of a gene. The fragment is then circularized by intramolecular ligation and used as a PCR template.

Another method which may be used is capture PCR which involves PCR amplification of DNA fragments adjacent to a known sequence in human and yeast artificial chromosome DNA (Lagerstrom, M. et al. (1991) PCR Methods Applic. 1:111–119). In this method, multiple restriction enzyme digestions and ligations may also be used to place an engineered double-stranded sequence into an unknown fragment of the DNA molecule before performing PCR.

Another method which may be used to retrieve unknown sequences is that of Parker, J. D. et al. (1991; Nucleic Acids Res. 19:3055–3060). Additionally, one may use PCR, nested primers, and PROMOTERFINDER libraries to walk genomic DNA (Clontech, Palo Alto, Calif.). This process avoids the need to screen libraries and is useful in finding intron/exon junctions.

When screening for full-length cDNAs, it is preferable to use libraries that have been size-selected to include larger cDNAs. Also, random-primed libraries are preferable, in that they will contain more sequences which contain the 5' regions of genes. Use of a randomly primed library may be especially preferable for situations in which an oligo d(T) library does not yield a full-length cDNA. Genomic libraries may be useful for extension of sequence into 5' non-transcribed regulatory regions.

Capillary electrophoresis systems which are commercially available may be used to analyze the size or confirm the nucleotide sequence of sequencing or PCR products. In particular, capillary sequencing may employ flowable polymers for electrophoretic separation, four different fluorescent dyes (one for each nucleotide) which are laser activated, and detection of the emitted wavelengths by a charge coupled device camera. Output/light intensity may be converted to electrical signal using appropriate software (e.g. GENOTYBER and SEQUENCE NAVIGATOR, Perkin Elmer) and the entire process from loading of samples to computer analysis and electronic data display may be computer controlled. Capillary electrophoresis is especially preferable for the sequencing of small pieces of DNA which might be present in limited amounts in a particular sample.

In another embodiment of the invention, polynucleotide sequences or fragments thereof which encode RABP may be used in recombinant DNA molecules to direct expression of RABP, fragments or functional equivalents thereof, in appropriate host cells. Due to the inherent degeneracy of the genetic code, other DNA sequences which encode substantially the same or a functionally equivalent amino acid sequence may be produced, and these sequences may be used to clone and express RABP.

As will be understood by those of skill in the art, it may be advantageous to produce RABP-encoding nucleotide sequences possessing non-naturally occurring codons. For example, codons preferred by a particular prokaryotic or eukaryotic host can be selected to increase the rate of protein expression or to produce an RNA transcript having desirable properties, such as a half-life which is longer than that of a transcript generated from the naturally occurring sequence.

The nucleotide sequences of the present invention can be engineered using methods generally known in the art in order to alter RABP encoding sequences for a variety of reasons, including but not limited to, alterations which modify the cloning, processing, and/or expression of the gene product. DNA shuffling by random fragmentation and PCR reassembly of gene fragments and synthetic oligonucleotides may be used to engineer the nucleotide sequences. For example, site-directed mutagenesis may be used to insert new restriction sites, alter glycosylation patterns, change codon preference, produce splice variants, introduce mutations, and so forth.

In another embodiment of the invention, natural, modified, or recombinant nucleic acid sequences encoding RABP may be ligated to a heterologous sequence to encode a fusion protein. For example, to screen peptide libraries for inhibitors of RABP activity, it may be useful to encode a chimeric RABP protein that can be recognized by a commercially available antibody. A fusion protein may also be engineered to contain a cleavage site located between the RABP encoding sequence and the heterologous protein sequence, so that RABP may be cleaved and purified away from the heterologous moiety.

In another embodiment, sequences encoding RABP may be synthesized, in whole or in part, using chemical methods well known in the art (see Caruthers, M. H. et al. (1980) Nucl. Acids Res. Symp. Ser. 215–223, Horn, T. et al. (1980) Nucl. Acids Res. Symp. Ser. 225–232). Alternatively, the protein itself may be produced using chemical methods to synthesize the amino acid sequence of RABP, or a fragment thereof. For example, peptide synthesis can be performed using various solid-phase techniques (Roberge, J. Y. et al. (1995) Science 269:202–204) and automated synthesis may be achieved, for example, using the ABI 43 1A Peptide Synthesizer (Perkin Elmer).

The newly synthesized peptide may be substantially purified by preparative high performance liquid chromatography (e.g., Creighton, T. (1983) *Proteins, Structures and Molecular Principles*, WH Freeman and Co., New York, N.Y.). The composition of the synthetic peptides may be confirmed by amino acid analysis or sequencing (e.g., the Edman degradation procedure; Creighton, supra). Additionally, the amino acid sequence of RABP, or any part thereof, may be altered during direct synthesis and/or combined using chemical methods with sequences from other proteins, or any part thereof, to produce a variant polypeptide.

In order to express a biologically active RABP, the nucleotide sequences encoding RABP or functional equivalents, may be inserted into appropriate expression vector, i.e., a vector which contains the necessary elements for the transcription and translation of the inserted coding sequence.

Methods which are well known to those skilled in the art may be used to construct expression vectors containing sequences encoding RABP and appropriate transcriptional and translational control elements. These methods include in vitro recombinant DNA techniques, synthetic techniques, and in vivo genetic recombination. Such techniques are described in Sambrook, J. et al. (1989) *Molecular Cloning, A Laboratory Manual*, Cold Spring Harbor Press, Plainview, N.Y., and Ausubel, F. M. et al. (1989) *Current Protocols in Molecular Biology*, John Wiley & Sons, New York, N.Y.

A variety of expression vector/host systems may be utilized to contain and express sequences encoding RABP. These include, but are not limited to, microorganisms such as bacteria transformed with recombinant bacteriophage, plasmid, or cosmid DNA expression vectors; yeast transformed with yeast expression vectors; insect cell systems infected with virus expression vectors (e.g., baculovirus); plant cell systems transformed with virus expression vectors (e.g., cauliflower mosaic virus, CaMV; tobacco mosaic virus, TMV) or with bacterial expression vectors (e.g., Ti or pBR322 plasmids); or animal cell systems. The invention is not limited by the host cell employed.

The "control elements" or "regulatory sequences" are those non-translated regions of the vector—enhancers, promoters, 5' and 3' untranslated regions—which interact with host cellular proteins to carry out transcription and translation. Such elements may vary in their strength and specificity. Depending on the vector system and host utilized, any number of suitable transcription and translation elements, including constitutive and inducible promoters, may be used. For example, when cloning in bacterial systems, inducible promoters such as the hybrid lacZ promoter of the BLUESCRIPT phagemid (Stratagene, LaJolla, CA) or PSPORTI plasmid (Gibco BRL) and the like may be used. The baculovirus polyhedrin promoter may be used in insect cells. Promoters or enhancers derived from the genomes of plant cells (e.g., heat shock, RUBISCO; and storage protein genes) or from plant viruses (e.g., viral promoters or leader sequences) may be cloned into the vector. In mammalian cell systems, promoters from mammalian genes or from mammalian viruses are preferable. If it is necessary to generate a cell line that contains multiple copies of the sequence encoding RABP, vectors based on SV40 or EBV may be used with an appropriate selectable marker.

In bacterial systems, a number of expression vectors may be selected depending upon the use intended for RABP. For example, when large quantities of RABP are needed for the induction of antibodies, vectors which direct high level expression of fusion proteins that are readily purified may be used. Such vectors include, but are not limited to, the multifunctional *E. coli* cloning and expression vectors such as BLUESCRIPT (Stratagene), in which the sequence encoding RABP may be ligated into the vector in frame with sequences for the amino-terminal Met and the subsequent 7 residues of β-galactosidase so that a hybrid protein is produced; pIN vectors (Van Heeke, G. and S. M. Schuster (1989) J. Biol. Chem. 264:5503–5509); and the like. pGEX vectors (Promega, Madison, Wis.) may also be used to express foreign polypeptides as fusion proteins with glutathione S-transferase (GST). In general, such fusion proteins are soluble and can easily be purified from lysed cells by adsorption to glutathione-agarose beads followed by elution in the presence of free glutathione. Proteins made in such systems may be designed to include heparin, thrombin, or factor XA protease cleavage sites so that the cloned polypeptide of interest can be released from the GST moiety at will.

In the yeast, *Saccharomyces cerevisiae*, a number of vectors containing constitutive or inducible promoters such as alpha factor, alcohol oxidase, and PGH may be used. For reviews, see Ausubel et al. (supra) and Grant et al. (1987) Methods Enzymol. 153:516–544.

In cases where plant expression vectors are used, the expression of sequences encoding RABP may be driven by any of a number of promoters. For example, viral promoters such as the 35S and 19S promoters of CaMV may be used alone or in combination with the omega leader sequence from TMV (Takamatsu, N. (1987) EMBO J. 6:307–311). Alternatively, plant promoters such as the small subunit of RUBISCO or heat shock promoters may be used (Coruzzi, G. et al. (1984) EMBO J. 3:1671–1680; Broglie, R. et al. (1984) Science 224:838–843; and Winter, J. et al. (1991) Results Probl. Cell Differ. 17:85–105). These constructs can be introduced into plant cells by direct DNA transformation or pathogen-mediated transfection. Such techniques are described in a number of generally available reviews (see, for example, Hobbs, S. or Murry, L. E. in McGraw Hill *Yearbook of Science and Technology* (1992) McGraw Hill, New York, N.Y.; pp. 191–196).

An insect system may also be used to express RABP. For example, in one such system, *Autographa californica* nuclear polyhedrosis virus (AcNPV) is used as a vector to express foreign genes in *Spodoptera frugiperda* cells or in Trichoplusia larvae. The sequences encoding RABP may be cloned into a non-essential region of the virus, such as the polyhedrin gene, and placed under control of the polyhedrin promoter. Successful insertion of RABP will render the polyhedrin gene inactive and produce recombinant virus lacking coat protein. The recombinant viruses may then be used to infect, for example, *S. frugiperda* cells or Trichoplusia larvae in which RABP may be expressed (Engelhard, E. K. et al. (1994) Proc. Nat. Acad. Sci. 91:3224–3227).

In mammalian host cells, a number of viral-based expression systems may be utilized. In cases where an adenovirus is used as an expression vector, sequences encoding RABP may be ligated into an adenovirus transcription/translation complex consisting of the late promoter and tripartite leader sequence. Insertion in a non-essential E1 or E3 region of the viral genome may be used to obtain a viable virus which is capable of expressing RABP in infected host cells (Logan, J. and Shenk, T. (1984) Proc. Natl. Acad. Sci. 81:3655–3659). In addition, transcription enhancers, such as the Rous sarcoma virus (RSV) enhancer, may be used to increase expression in mammalian host cells.

Human artificial chromosomes (HACs) may also be employed to deliver larger fragments of DNA than can be contained and expressed in a plasmid. HACs of 6 to 10M are constructed and delivered via conventional delivery methods (liposomes, polycationic amino polymers, or vesicles) for therapeutic purposes.

Specific initiation signals may also be used to achieve more efficient translation of sequences encoding RABP. Such signals include the ATG initiation codon and adjacent sequences. In cases where sequences encoding RABP, its initiation codon, and upstream sequences are inserted into the appropriate expression vector, no additional transcriptional or translational control signals may be needed. However, in cases where only coding sequence, or a fragment thereof, is inserted, exogenous translational control signals including the ATG initiation codon should be provided. Furthermore, the initiation codon should be in the correct reading frame to ensure translation of the entire insert. Exogenous translational elements and initiation codons may be of various origins, both natural and synthetic. The efficiency of expression may be enhanced by the inclusion of enhancers which are appropriate for the particular cell system which is used, such as those described in the literature (Scharf, D. et al. (1994) Results Probl. Cell Differ. 20:125–162).

In addition, a host cell strain may be chosen for its ability to modulate the expression of the inserted sequences or to process the expressed protein in the desired fashion. Such modifications of the polypeptide include, but are not limited to, acetylation, carboxylation, glycosylation, phosphorylation, lipidation, and acylation. Post-translational processing which cleaves a "prepro" form of the protein may also be used to facilitate correct insertion, folding and/or function. Different host cells which have specific cellular machinery and characteristic mechanisms for post-translational activities (e.g., CHO, HeLa, MDCK, HEK293, and W138), are available from the American Type Culture Collection (ATCC; Bethesda, Md.) and may be chosen to ensure the correct modification and processing of the foreign protein.

For long-term, high-yield production of recombinant proteins, stable expression is preferred. For example, cell lines which stably express RABP may be transformed using expression vectors which may contain viral origins of replication and/or endogenous expression elements and a selectable marker gene on the same or on a separate vector. Following the introduction of the vector, cells may be allowed to grow for 1–2 days in an enriched media before they are switched to selective media The purpose of the selectable marker is to confer resistance to selection, and its presence allows growth and recovery of cells which successfully express the introduced sequences. Resistant clones of stably transformed cells may be proliferated using tissue culture techniques appropriate to the cell type.

Any number of selection systems may be used to recover transformed cell lines. These include, but are not limited to, the herpes simplex virus thymidine kinase (Wigler, M. et al. (1977) Cell 11:223–32) and adenine phosphoribosyltransferase (Lowy, I. et al. (1980) Cell 22:817–23) genes which can be employed in tk$^-$ or aprt$^-$ cells, respectively. Also, antimetabolite, antibiotic or herbicide resistance can be used as the basis for selection; for example, dhfr which confers resistance to methotrexate (Wigler, M. et al. (1980) Proc. Natl. Acad. Sci. 77:3567–70); npt, which confers resistance to the aminoglycosides, neomycin and G-418 (Colbere-Garapin, F. et al (1981) J. Mol. Biol. 150–14), and als or pat, which confer resistance to chlorsulfuron and phosphinotricin acetyltransferase, respectively (Murry, supra). Additional selectable genes have been described, for example, trpB, which allows cells to utilize indole in place of tryptophan, or hisD, which allows cells to utilize histinol in place of histidine (Hartman, S. C. and R. C. Mulligan (1988) Proc. Natl. Acad. Sci. 85:8047–51). Recently, the use of visible markers has gained popularity with such markers as anthocyanins, β glucuronidase and its substrate GUS, and luciferase and its substrate luciferin, being widely used not only to identify transformants, but also to quantify the amount of transient or stable protein expression attributable to a specific vector system (Rhodes, C. A. et al. (1995) Methods Mol. Biol. 55:121–131).

Although the presence/absence of marker gene expression suggests that the gene of interest is also present, its presence and expression may need to be confirmed. For example, if the sequence encoding RABP is inserted within a marker gene sequence, transformed cells containing sequences encoding RABP can be identified by the absence of marker gene function. Alternatively, a marker gene can be placed in tandem with a sequence encoding RABP under the control of a single promoter. Expression of the marker gene in response to induction or selection usually indicates expression of the tandem gene as well.

Alternatively, host cells which contain the nucleic acid sequence encoding RABP and express RABP may be identified by a variety of procedures known to those of skill in the art. These procedures include, but are not limited to, DNA-DNA or DNA-RNA hybridizations and protein bioassay or immunoassay techniques which include membrane, solution, or chip based technologies for the detection and/or quantification of nucleic acid or protein.

The presence of polynucleotide sequences encoding RABP can be detected by DNA-DNA or DNA-RNA hybridization or amplification using probes or fragments or fragments of polynucleotides encoding RABP. Nucleic acid amplification based assays involve the use of oligonucleotides or oligomers based on the sequences encoding RABP to detect transformants containing DNA or RNA encoding RABP.

A variety of protocols for detecting and measuring the expression of RABP, using either polyclonal or monoclonal antibodies specific for the protein are known in the art. Examples include enzyme-linked immunosorbent assay (ELISA), radioimmunoassay (RIA), and fluorescence activated cell sorting (FACS). A two-site, monoclonal-based immunoassay utilizing monoclonal antibodies reactive to two non-interfering epitopes on RABP is preferred, but a competitive binding assay may be employed. These and other assays are described, among other places, in Hampton, R. et al. (1990; *Serological Methods, a Laboratory Manual*, APS Press, St Paul, Minn.) and Maddox, D. E. et al. (1983; J. Exp. Med. 158:1211–1216).

A wide variety of labels and conjugation techniques are known by those skilled in the art and may be used in various nucleic acid and amino acid assays. Means for producing labeled hybridization or PCR probes for detecting sequences related to polynucleotides encoding RABP include oligolabeling, nick translation, end-labeling or PCR amplification using a labeled nucleotide. Alternatively, the sequences encoding RABP, or any fragments thereof may be cloned into a vector for the production of an mRNA probe. Such vectors are known in the art, are commercially available, and may be used to synthesize RNA probes in vitro by addition of an appropriate RNA polymerase such as T7, T3, or SP6 and labeled nucleotides. These procedures may be conducted using a variety of commercially available kits (Pharmacia & Upjohn, (Kalamazoo, Mich.); Promega (Madison Wis.); and U.S. Biochemical Corp., Cleveland, Ohio.). Suitable reporter molecules or labels, which may be used for ease of detection, include radionuclides, enzymes, fluorescent, chemiluminescent, or chromogenic agents as well as substrates, cofactors, inhibitors, magnetic particles, and the like.

Host cells transformed with nucleotide sequences encoding RABP may be cultured under conditions suitable for the expression and recovery of the protein from cell culture. The protein produced by a transformed cell may be secreted or contained intracellularly depending on the sequence and/or the vector used. As will be understood by those of skill in the art, expression vectors containing polynucleotides which encode RABP may be designed to contain signal sequences which direct secretion of RABP through a prokaryotic or eukaryotic cell membrane. Other constructions may be used to join sequences encoding RABP to nucleotide sequence encoding a polypeptide domain which will facilitate purification of soluble proteins. Such purification facilitating domains include, but are not limited to, metal chelating peptides such as histidine-tryptophan modules that allow purification on immobilized metals, protein A domains that allow purification on immobilized immunoglobulin, and the domain utilized in the FLAGS extension/affinity purification system (Immunex Corp., Seattle, Wash.). The inclusion of cleavable linker sequences such as those specific for Factor XA or enterokinase (Invitrogen, San Diego, Calif.) between the purification domain and RABP may be used to facilitate purification. One such expression vector provides for expression of a fusion protein containing RABP and a nucleic acid encoding 6 histidine residues preceding a thioredoxin or an enterokinase cleavage site. The histidine residues facilitate purification on IMAC (immobilized metal ion affinity chromatography) as described in Porath, J. et al. (1992, Prot. Exp. Purif. 3: 263–281) while the enterokinase cleavage site provides a means for purifying RABP from the fusion protein. A discussion of vectors which contain fusion proteins is provided in Kroll, D. J. et al. (1993; DNA Cell Biol. 12:441–453).

In addition to recombinant production, fragments of RABP may be produced by direct peptide synthesis using solid-phase techniques (Merrifield J. (1963) J. Am. Chem. Soc. 85:2149–2154). Protein synthesis may be performed using manual techniques or by automation. Automated synthesis may be achieved, for example, using Applied Biosystems 431A Peptide Synthesizer (Perkin Elmer). Various fragments of RABP may be chemically synthesized separately and combined using chemical methods to produce the full length molecule.

THERAPEUTICS

Chemical and structural homology exists between RABP-1 and a mouse Rab24 (GI 438164; SEQ ID NO:7), between RABP-2 and a rat Rab1B (GI 57006; SEQ ID NO:8), and between RABP-3 and a rat Rab28 (GI 1154901; SEQ ID NO:9). Northern analysis shows that the expression of RABP (SEQ ID NO:1, SEQ ID NO:3, or SEQ ID NO:5) is associated with cancer and fetal/infant development. Therapeutic uses for all three polypeptides are described collectively below.

During fetal development, decreased expression of RABP may cause an increase in apoptosis with no adverse effects to the subject. However, in other situations and in adults, decreased expression of RABP may cause an increase in apoptosis which is detrimental. Therefore, in one embodiment, RABP or a fragment or derivative thereof may be administered to a subject to prevent or treat a disorder associated with an increase in apoptosis. Such disorders include, but are not limited to, AIDS and other infectious or genetic immunodeficiencies, neurodegenerative diseases such as Alzheimer's disease, Parkinson's disease, amyotrophic lateral sclerosis, retinitis pigmentosa, and cerebellar degeneration, myelodysplastic syndromes such as aplastic anemia, ischemic injuries such as myocardial infarction, stroke, and reperfusion injury, toxin-induced diseases such as alcohol-induced liver damage, cirrhosis, and lathyrism, wasting diseases such as cachexia, viral infections such as those caused by hepatitis B and C, and osteoporosis.

In another embodiment, an agonist which is specific for RABP may be used to prevent or treat a disorder associated with increased apoptosis including, but not limited to, those listed above.

In still another embodiment, a vector capable of expressing RABP (SEQ ID NO:1,), or a fragment or a derivative thereof, may be used to prevent or treat a disorder associated with increased apoptosis including, but not limited to, those listed above.

In a further embodiment, RABP or a fragment or derivative thereof may be added to cells to stimulate cell proliferation. In particular, RABP may be added to a cell or cells in vivo using delivery mechanisms such as liposomes, viral based vectors, or electroinjection for the purpose of promoting regeneration or cell differentiation of the cell or cells. In addition, RABP may be added to a cell, cell line, tissue or organ culture in vitro or ex vivo to stimulate cell proliferation for use in heterologous or autologous transplantation. In some cases, the cell will have been selected for its ability to fight an infection or a cancer or to correct a genetic defect in a disease such as sickle cell anemia, β thalassemia, cystic fibrosis, or Huntington's chorea.

In another further embodiment, an agonist which is specific for RABP may be administered to a cell to stimulate cell proliferation, as described above.

In another further embodiment, a vector capable of expressing RABP, or a fragment or a derivative thereof, may be administered to a cell or cells in vivo using delivery mechanisms, or to a cell to stimulate cell proliferation, as described above.

Increased expression of RABP appears to be associated with increased cell proliferation. Therefore, in one embodiment, an antagonist of RABP, or a fragment or a derivative thereof, may be administered to a subject to prevent or treat a disorder associated with cell proliferation. Such disorders include various types of cancer including, but not limited to, adenocarcinoma, leukemia, lymphoma, melanoma, myeloma, sarcoma, and teratocarcinoma, and, in particular, cancers of the adrenal gland, bladder, bone, bone marrow, brain, breast; cervix, gall bladder, ganglia, gastrointestinal tract, heart, kidney, liver, lung, muscle, ovary, pancreas, parathyroid, penis, prostate, salivary glands, skin, spleen, testis, thymus, thyroid, and uterus. In one aspect, an antibody specific for RABP may be used directly as an antagonist, or indirectly as a targeting or delivery mechanism for bringing a pharmaceutical agent to cells or tissue which express RABP.

In still another embodiment, a vector expressing the complement of the polynucleotide encoding RABP, or a fragment or a derivative thereof, may be administered to a subject to prevent or treat a disorder associated with cell proliferation including, but not limited to, the types of cancer listed above.

In another embodiment, an antagonist of RABP, or a fragment or a derivative thereof, may be administered to a subject to prevent or treat inflammation. Disorders associated with inflammation include, but are not limited to, Addison's disease, adult respiratory distress syndrome, allergies, anemia, asthma, atherosclerosis, bronchitis, cholecystitus, Crohn's disease, ulcerative colitis, atopic dermatitis, dermatomyositis, diabetes mellitus, emphysema, atrophic gastritis, glomerulonephritis, gout, Graves' disease, hypereosinophilia, irritable bowel syndrome, lupus erythematosus, multiple sclerosis, myasthenia gravis, myocardial or pericardial inflammation,osteoarthritis, osteoporosis, pancreatitis, polymyositis, rheumatoid arthritis, scleroderma, Sjöbgren's syndrome, and autoimmune thyroiditis; complications of cancer, hemodialysis, extracorporeal circulation; viral, bacterial, fungal, parasitic, protozoal, and helminthic infections and trauma. In one aspect, an antibody specific for RABP may be used directly as an antagonist, or indirectly as a targeting or delivery mechanism for bringing a pharmaceutical agent to cells or tissue which express RABP.

In still another embodiment, a vector expressing the complement of the polynucleotide encoding RABP, or a fragment or a derivative thereof, may be administered to a subject to prevent or treat inflammation associated with any disorder including, but not limited to, those listed above.

In other embodiments, any of the proteins, antagonists, antibodies, agonists, complementary sequences or vectors of the invention may be administered in combination with other appropriate therapeutic agents. Selection of the appropriate agents for use in combination therapy may be made by one of ordinary skill in the art, according to conventional pharmaceutical principles. The combination of therapeutic agents may act synergistically to effect the treatment or prevention of the various disorders described above. Using this approach, one may be able to achieve therapeutic efficacy with lower dosages of each agent, thus reducing the potential for adverse side effects.

An antagonist of RABP may be produced using methods which are generally known in the art. In particular, purified RABP may be used to produce antibodies or to screen libraries of pharmaceutical agents to identify those which specifically bind RABP.

Antibodies to RABP may be generated using methods that are well known in the art. Such antibodies may include, but are not limited to, polyclonal, monoclonal, chimeric, single chain, Fab fragments, and fragments produced by a Fab expression library. Neutralizing antibodies, (i.e., those which inhibit dimer formation) are especially preferred for therapeutic use.

For the production of antibodies, various hosts including goats, rabbits, rats, mice, humans, and others, may be immunized by injection with RABP or any fragment or oligopeptide thereof which has immunogenic properties. Depending on the host species, various adjuvants may be used to increase immunological response. Such adjuvants include, but are not limited to, Freund's, mineral gels such as aluminum hydroxide, and surface active substances such as lysolecithin, pluronic polyols, polyanions, peptides, oil emulsions, keyhole limpet hemocyanin, and dinitrophenol. Among adjuvants used in humans, BCG (bacilli Calmette-Guerin) and *Corynebacterium paryum* are especially preferable.

It is preferred that the oligopeptides, peptides, or fragments used to induce antibodies to RABP have an amino acid sequence consisting of at least five amino acids and more preferably at least 10 amino acids. It is also preferable that they are identical to a portion of the amino acid sequence of the natural protein, and they may contain the entire amino acid sequence of a small, naturally occurring molecule. Short stretches of RABP amino acids may be fused with those of another protein such as keyhole limpet hemocyanin and antibody produced against the chimeric molecule.

Monoclonal antibodies to RABP may be prepared using any technique which provides for the production of antibody molecules by continuous cell lines in culture. These include, but are not limited to, the hybridoma technique, the human B-cell hybridoma technique, and the EBV-hybridoma technique (Kohler, G. et al. (1975) Nature 256:495–497; Kozbor, D. et al. (1985) J. Immunol. Methods 81:31–42; Cote, R. J. et al. (1983) Proc. Natl. Acad. Sci. 80:2026–2030; Cole, S. P. et al. (1984) Mol. Cell Biol. 62:109–120).

In addition, techniques developed for the production of "chimeric antibodies", the splicing of mouse antibody genes to human antibody genes to obtain a molecule with appropriate antigen specificity and biological activity can be used (Morrison, S. L. et al. (1984) Proc. Natl. Acad. Sci. 81:6851–6855; Neuberger, M. S. et al. (1984) Nature 312:604–608; Takeda, S. et al. (1985) Nature 314:452–454). Alternatively, techniques described for the production of single chain antibodies may be adapted, using methods known in the art, to produce RABP-specific single chain antibodies. Antibodies with related specificity, but of distinct idiotypic composition, may be generated by chain shuffling from random combinatorial immunoglobuin libraries (Burton D. R. (1991) Proc. Natl. Acad. Sci. 88:11120–3).

Antibodies may also be produced by inducing in vivo production in the lymphocyte population or by screening immunoglobulin libraries or panels of highly specific binding reagents as disclosed in the literature (Orlandi, R. et al. (1989) Proc. Natl. Acad. Sci. 86: 3833–3837; Winter, G. et al. (1991) Nature 349:293–299).

Antibody fragments which contain specific binding sites for RABP may also be generated. For example, such fragments include, but are not limited to, the F(ab')2 fragments which can be produced by pepsin digestion of the antibody molecule and the Fab fragments which can be generated by reducing the disulfide bridges of the F(ab')2 fragments. Alternatively, Fab expression libraries may be constructed to allow rapid and easy identification of monoclonal Fab fragments with the desired specificity (Huse, W. D. et al. (1989) Science 254:1275–1281).

Various immunoassays may be used for screening to identify antibodies having the desired specificity. Numerous protocols for competitive binding or immunoradiometric assays using either polyclonal or monoclonal antibodies with established specificities are well known in the art. Such immunoassays typically involve the measurement of complex formation between RABP and its specific antibody. A two-site, monoclonal-based immunoassay utilizing monoclonal antibodies reactive to two non-interfering RABP epitopes is preferred, but a competitive binding assay may also be employed (Maddox, supra).

In another embodiment of the invention, the polynucleotides encoding RABP, or any fragment or complement thereof, may be used for therapeutic purposes. In one aspect, the complement of the polynucleotide encoding RABP may be used in situations in which it would be desirable to block the transcription of the mRNA. In particular, cells may be transformed with sequences complementary to polynucleotides encoding RABP. Thus, complementary molecules or fragments may be used to modulate RABP activity, or to achieve regulation of gene function. Such technology is now well known in the art, and sense or antisense oligonucleotides or larger fragments, can be designed from various locations along the coding or control regions of sequences encoding RABP.

Expression vectors derived from retroviruses, adenovirus, herpes or vaccinia viruses, or from various bacterial plasmids may be used for delivery of nucleotide sequences to the targeted organ, tissue or cell population. Methods which are well known to those skilled in the art can be used to construct vectors which will express nucleic acid sequence which is complementary to the polynucleotides of the gene encoding RABP. These techniques are described both in Sambrook et al. (supra) and in Ausubel et al. (supra).

Genes encoding RABP can be turned off by transforming a cell or tissue with expression vectors which express high levels of a polynucleotide or fragment thereof which encodes RABP. Such constructs may be used to introduce untranslatable sense or antisense sequences into a cell. Even in the absence of integration into the DNA, such vectors may continue to transcribe RNA molecules until they are disabled by endogenous nucleases. Transient expression may last for a month or more with a non-replicating vector and even longer if appropriate replication elements are part of the vector system.

As mentioned above, modifications of gene expression can be obtained by designing complementary sequences or antisense molecules (DNA, RNA, or PNA) to the control, 5' or regulatory regions of the gene encoding RABP (signal sequence, promoters, enhancers, and introns). Oligonucleotides derived from the transcription initiation site, e.g., between positions −10 and +10 from the start site, are preferred. Similarly, inhibition can be achieved using "triple helix" base-pairing methodology. Triple helix pairing is useful because it causes inhibition of the ability of the double helix to open sufficiently for the binding of polymerases, transcription factors, or regulatory molecules. Recent therapeutic advances using triplex DNA have been described in the literature (Gee, J. E. et al. (1994) In: Huber, B. E. and B. I. Carr, *Molecular and Immunologic Approaches*, Futura Publishing Co., Mt. Kisco, N.Y.). The complementary sequence or antisense molecule may also be designed to block translation of mRNA by preventing the transcript from binding to ribosomes.

Ribozymes, enzymatic RNA molecules, may also be used to catalyze the specific cleavage of RNA. The mechanism of ribozyme action involves sequence-specific hybridization of the ribozyme molecule to complementary target RNA, followed by endonucleolytic cleavage. Examples which may be used include engineered hammerhead motif ribozyme molecules that can specifically and efficiently catalyze endonucleolytic cleavage of sequences encoding RABP.

Specific ribozyme cleavage sites within any potential RNA target are initially identified by scanning the target molecule for ribozyme cleavage sites which include the following sequences: GUA, GUU, and GUC. Once identified, short RNA sequences of between 15 and 20 ribonucleotides corresponding to the region of the target gene containing the cleavage site may be evaluated for secondary structural features which may render the oligonucleotide inoperable. The suitability of candidate targets may also be evaluated by testing accessibility to hybridization with complementary oligonucleotides using ribonuclease protection assays.

Complementary ribonucleic acid molecules and ribozymes of the invention may be prepared by any method known in the art for the synthesis of nucleic acid molecules. These include techniques for chemically synthesizing oligonucleotides such as solid phase phosphoramidite chemical synthesis. Alternatively, RNA molecules may be generated by in vitro and in vivo transcription of DNA sequences encoding RABP. Such DNA sequences may be incorporated into a wide variety of vectors with suitable RNA polymerase promoters such as T7 or SP6. Alternatively, these cDNA constructs that synthesize complementary RNA constitutively or inducibly can be introduced into cell lines, cells, or tissues.

RNA molecules may be modified to increase intracellular stability and half-life. Possible modifications include, but are not limited to, the addition of flanking sequences at the 5' and/or 3' ends of the molecule or the use of phosphorothioate or 2' O-methyl rather than phosphodiesterase linkages within the backbone of the molecule. This concept is inherent in the production of PNAs and can be extended in all of these molecules by the inclusion of nontraditional bases such as inosine, queosine, and wybutosine, as well as acetyl-, methyl-, thio-, and similarly modified forms of adenine, cytidine, guanine, thymine, and uridine which are not as easily recognized by endogenous endonucleases.

Many methods for introducing vectors into cells or tissues are available and equally suitable for use in vivo, in vitro, and a vivo. For ex vivo therapy, vectors may be introduced into stem cells taken from the patient and clonally propagated for autologous transplant back into that same patient. Delivery by transfection, by liposome injections or polycationic amino polymers (Goldman, C. K. et at. (1997) Nature Biotechnology 15:462–66; incorporated herein by reference) may be achieved using methods which are well known in the art.

Any of the therapeutic methods described above may be applied to any subject in need of such therapy, including, for example, mammals such as dogs, cats, cows, horses, rabbits, monkeys, and most preferably, humans.

An additional embodiment of the invention relates to the administration of a pharmaceutical composition, in conjunction with a pharmaceutically acceptable carrier, for any of the therapeutic effects discussed above. Such pharmaceutical compositions may consist of RABP, antibodies to RABP, mimetics, agonists, antagonists, or inhibitors of RABP. The compositions may be administered alone or in combination with at least one other agent, such as stabilizing compound, which may be administered in any sterile, biocompatible pharmaceutical carrier, including, but not limited to, saline, buffered saline, dextrose, and water. The compositions may be administered to a patient alone, or in combination with other agents, drugs or hormones.

The pharmaceutical compositions utilized in this invention may be administered by any number of routes including, but not limited to, oral, intravenous, intramuscular, intra-arterial, intramedullary, intrathecal, intraventricular, transdermal, subcutaneous, intraperitoneal, intranasal, enteral, topical, sublingual, or rectal means.

In addition to the active ingredients, these pharmaceutical compositions may contain suitable pharmaceutically-acceptable carriers comprising excipients and auxiliaries which facilitate processing of the active compounds into preparations which can be used pharmaceutically. Further details on techniques for formulation and administration may be found in the latest edition of *Remington's Pharmaceutical Sciences* (Maack Publishing Co., Easton, Pa.).

Pharmaceutical compositions for oral administration can be formulated using pharmaceutically acceptable carriers well known in the art in dosages suitable for oral administration. Such carriers enable the pharmaceutical compositions to be formulated as tablets, pills, dragees, capsules, liquids, gels, syrups, slurries, suspensions, and the like, for ingestion by the patient.

Pharmaceutical preparations for oral use can be obtained through combination of active compounds with solid excipient, optionally grinding a resulting mixture, and processing the mixture of granules, after adding suitable auxiliaries, if desired, to obtain tablets or dragee cores. Suitable excipients are carbohydrate or protein fillers, such as sugars, including lactose, sucrose, mannitol, or sorbitol; starch from corn, wheat, rice, potato, or other plants; cellulose, such as methyl cellulose, hydroxypropylmethylcellulose, or sodium carboxymethylcellulose; gums including arabic and tragacanth; and proteins such as gelatin and collagen. If desired, disintegrating or solubilizing agents may be added, such as the cross-linked polyvinyl pyrrolidone, agar, alginic acid, or a salt thereof, such as sodium alginate.

Dragee cores may be used in conjunction with suitable coatings, such as concentrated sugar solutions, which may also contain gum arabic, talc, polyvinylpyrrolidone, carbopol gel, polyethylene glycol, and/or titanium dioxide, lacquer solutions, and suitable organic solvents or solvent mixtures. Dyestuffs or pigments may be added to the tablets or dragee coatings for product identification or to characterize the quantity of active compound, i.e., dosage.

Pharmaceutical preparations which can be used orally include push-fit capsules made of gelatin, as well as soft, sealed capsules made of gelatin and a coating, such as glycerol or sorbitol. Push-fit capsules can contain active ingredients mixed with a filler or binders, such as lactose or starches, lubricants, such as talc or magnesium stearate, and, optionally, stabilizers. In soft capsules, the active compounds may be dissolved or suspended in suitable liquids, such as fatty oils, liquid, or liquid polyethylene glycol with or without stabilizers.

Pharmaceutical formulations suitable for parenteral administration may be formulated in aqueous solutions, preferably in physiologically compatible buffers such as Hanks' solution, Ringer's solution, or physiologically buffered saline. Aqueous injection suspensions may contain substances which increase the viscosity of the suspension, such as sodium carboxymethyl cellulose, sorbitol, or dextran. Additionally, suspensions of the active compounds may be prepared as appropriate oily injection suspensions. Suitable lipophilic solvents or vehicles include fatty oils such as sesame oil, or synthetic fatty acid esters, such as ethyl oleate or triglycerides, or liposomes. Non-lipid polycationic amino polymers may also be used for delivery. Optionally, the suspension may also contain suitable stabilizers or agents which increase the solubility of the compounds to allow for the preparation of highly concentrated solutions.

For topical or nasal administration, penetrants appropriate to the particular barrier to be permeated are used in the formulation. Such penetrants are generally known in the art.

The pharmaceutical compositions of the present invention may be manufactured in a manner that is known in the art, e.g., by means of conventional mixing, dissolving, granulating, dragee-making, levigating, emulsifying, encapsulating, entrapping, or lyophilizing processes.

The pharmaceutical composition may be provided as a salt and can be formed with many acids, including but not limited to, hydrochloric, sulfuric, acetic, lactic, tartaric, malic, succinic, etc. Salts tend to be more soluble in aqueous or other protonic solvents than are the corresponding free base forms. In other cases, the preferred preparation may be a lyophilized powder which may contain any or all of the following: 1–50 mM histidine, 0.1%–2% sucrose, and 2–7% mannitol, at a pH range of 4.5 to 5.5, that is combined with buffer prior to use.

After pharmaceutical compositions have been prepared, they can be placed in an appropriate container and labeled for treatment of an indicated condition. For administration of RABP, such labeling would include amount, frequency, and method of administration.

Pharmaceutical compositions suitable for use in the invention include compositions wherein the active ingredients are contained in an effective amount to achieve the intended purpose. The determination of an effective dose is well within the capability of those skilled in the art.

For any compound, the therapeutically effective dose can be estimated initially either in cell culture assays, e.g., of neoplastic cells, or in animal models, usually mice, rabbits, dogs, or pigs. The animal model may also be used to determine the appropriate concentration range and route of administration. Such information can then be used to determine useful doses and routes for administration in humans.

A therapeutically effective dose refers to that amount of active ingredient, for example RABP or fragments thereof, antibodies of RABP, agonists, antagonists or inhibitors of RABP, which ameliorates the symptoms or condition. Therapeutic efficacy and toxicity may be determined by standard pharmaceutical procedures in cell cultures or experimental animals, e.g., ED50 (the dose therapeutically effective in 50% of the population) and LD50 (the dose lethal to 50% of the population). The dose ratio between therapeutic and toxic effects is the therapeutic index, and it can be expressed as the ratio, ED50/LD50. Pharmaceutical compositions which exhibit large therapeutic indices are preferred. The data obtained from cell culture assays and animal studies is used in formulating a range of dosage for human use. The dosage contained in such compositions is preferably within a range of circulating concentrations that include the ED50 with little or no toxicity. The dosage varies within this range depending upon the dosage form employed, sensitivity of the patient, and the route of administration.

The exact dosage will be determined by the practitioner, in light of factors related to the subject that requires treatment. Dosage and administration are adjusted to provide sufficient levels of the active moiety or to maintain the desired effect. Factors which may be taken into account include the severity of the disease state, general health of the subject, age, weight, and gender of the subject, diet, time and frequency of administration, drug combination(s), reaction sensitivities, and tolerance/response to therapy. Long-acting pharmaceutical compositions may be administered every 3 to 4 days, every week, or once every two weeks depending on half-life and clearance rate of the particular formulation.

Normal dosage amounts may vary from 0.1 to 100,000 micrograms, up to a total dose of about 1 g, depending upon the route of administration. Guidance as to particular dosages and methods of delivery is provided in the literature and generally available to practitioners in the art. Those skilled in the art will employ different formulations for nucleotides than for proteins or their inhibitors. Similarly, delivery of polynucleotides or polypeptides will be specific to particular cells, conditions, locations, etc.

DIAGNOSTICS

In another embodiment, antibodies which specifically bind RABP may be used for the diagnosis of conditions or diseases characterized by expression of RABP, or in assays to monitor patients being treated with RABP, agonists, antagonists or inhibitors. The antibodies useful for diagnostic purposes may be prepared in the same manner as those described above for therapeutics. Diagnostic assays for RABP include methods which utilize the antibody and a label to detect RABP in human body fluids or extracts of cells or tissues. The antibodies may be used with or without modification, and may be labeled by joining them, either covalently or non-covalently, with a reporter molecule. A wide variety of reporter molecules which are known in the art may be used, several of which are described above.

A variety of protocols including ELISA, RIA, and FACS for measuring RABP are known in the art and provide a basis for diagnosing altered or abnormal levels of RABP expression. Normal or standard values for RABP expression are established by combining body fluids or cell extracts taken from normal mammalian subjects, preferably human, with antibody to RABP under conditions suitable for complex formation The amount of standard complex formation may be quantified by various methods, but preferably by photometric means. Quantities of RABP expressed in subjects samples, control and disease, from biopsied tissues are compared with the standard values. Deviation between standard and subject values establishes the parameters for diagnosing disease.

In another embodiment of the invention, the polynucleotides encoding RABP may be used for diagnostic purposes. The polynucleotides which may be used include oligonucleotide sequences, complementary RNA and DNA molecules, and PNAs. The polynucleotides may be used to detect and quantitate gene expression in biopsied tissues in which expression of RABP may be correlated with disease. The diagnostic assay may be used to distinguish between absence, presence, and excess expression of RABP, and to monitor regulation of RABP levels during therapeutic intervention.

In one aspect, hybridization with PCR probes which are capable of detecting polynucleotide sequences, including genomic sequences, encoding RABP or closely related molecules, may be used to identify nucleic acid sequences which encode RABP. The specificity of the probe, whether it is made from a highly specific region, e.g., 10 unique nucleotides in the 5' regulatory region, or a less specific region, e.g., especially in the 3' coding region, and the stringency of the hybridization or amplification (maximal, high, intermediate, or low) will determine whether the probe identifies only naturally occurring sequences encoding RABP, alleles, or related sequences.

Probes may also be used for the detection of related sequences, and should preferably contain at least 50% of the nucleotides from any of the RABP encoding sequences. The hybridization probes of the subject invention may be DNA or RNA and derived from the nucleotide sequence of SEQ ID NO:2, SEQ ID NO:4, SEQ ID NO:6, or from genomic sequence including promoter, enhancer elements, and introns of the naturally occurring RABP.

Means for producing specific hybridization probes for DNAs encoding RABP include the cloning of nucleic acid sequences encoding RABP or RABP derivatives into vectors for the production of mRNA probes. Such vectors are known in the art, commercially available, and may be used to synthesize RNA probes in vitro by means of the addition of the appropriate RNA polymerases and the appropriate labeled nucleotides. Hybridization probes may be labeled by a variety of reporter groups, for example, radionuclides such as 32P or 35S, or enzymatic labels, such as alkaline phosphatase coupled to the probe via avidin/biotin coupling systems, and the like.

Polynucleotide sequences encoding RABP may be used for the diagnosis of conditions or disorders which are associated with expression of RABP. Examples of such conditions or disorders include, but are not limited to, disorders associated with cell proliferation such as adenocarcinoma, leukemia, lymphoma, melanoma, myeloma, sarcoma, and teratocarcinoma, and particularly, cancers of the adrenal gland, bladder, bone, bone marrow, brain, breast, cervix, gall bladder, ganglia, gastrointestinal tract, heart, kidney, liver, lung, muscle, ovary, pancreas, parathyroid, penis, prostate, salivary glands, skin, spleen, testis, thymus, thyroid, and uterus; disorders with associated inflammation such as Addison's disease, adult respiratory distress syndrome, allergies, anemia, asthma, atherosclerosis, bronchitis, cholecystitus, Crohn's disease, ulcerative colitis, atopic dermatitis, dermatomyositis, diabetes mellitus, emphysema, atrophic gastritis, glomerulonephritis, gout, Graves' disease, hypereosinophilia, irritable bowel syndrome, lupus erythematosus, multiple sclerosis, myasthenia gravis, myocardial or pericardial inflammation, osteoarthritis, osteoporosis, pancreatitis, polymyositis, rheumatoid arthritis, scleroderma, Sjögren's syndrome, and autoimmune thyroiditis; complications of cancer, hemodialysis, extracorporeal circulation; viral, bacterial, fungal, parasitic, protozoal, and helminthic infections and trauma; disorders with associated apoptosis such as AIDS and other infectious or genetic immunodeficiencies, neurodegenerative diseases such as Alzheimer's disease, Parkinson's disease, amyotrophic lateral sclerosis, retinitis pigmentosa, and cerebellar degeneration, myelodysplastic syndromes such as aplastic anemia, ischemic injuries such as myocardial infarction, stroke, and reperfusion injury, toxin-induced diseases such as alcohol- induced liver damage, cirrhosis, and lathyrism, wasting diseases such as cachexia, viral infections such as those caused by hepatitis B and C, and osteoporosis. The polynucleotide sequences encoding RABP may be used in Southern or northern analysis, dot blot, or other membrane-based technologies; in PCR technologies; or in dipstick, pin, ELISA assays or microarrays utilizing fluids or tissues from patient biopsies to detect altered RABP expression. Such qualitative or quantitative methods are well known in the art.

In a particular aspect, the nucleotide sequences encoding RABP may be useful in assays that detect activation or induction of various cancers, particularly those mentioned above. The nucleotide sequences encoding RABP may be labeled by standard methods, and added to a fluid or tissue sample from a patient under conditions suitable for the formation of hybridization complexes. After a suitable incubation period, the sample is washed and the signal is quantitated and compared with a standard value. If the amount of signal in the biopsied or extracted sample is significantly altered from that of a comparable control sample, the nucleotide sequences have hybridized with nucleotide sequences in the sample, and the presence of altered levels of nucleotide sequences encoding RABP in the sample indicates the presence of the associated disease. Such assays may also be used to evaluate the efficacy of a particular therapeutic treatment regimen in animal studies, in clinical trials, or in monitoring the treatment of an individual patient.

In order to provide a basis for the diagnosis of disease associated with expression of RABP, a normal or standard profile for expression is established. This may be accomplished by combining body fluids or cell extracts taken from normal subjects, either animal or human, with a sequence, or a fragment thereof, which encodes RABP, under conditions suitable for hybridization or amplification. Standard hybridization may be quantified by comparing the values obtained from normal subjects with those from an experiment where a known amount of a substantially purified polynucleotide is used. Standard values obtained from normal samples may be compared with values obtained from samples from patients who are symptomatic for disease. Deviation between standard and subject values is used to establish the presence of disease.

Once disease is established and a treatment protocol is initiated, hybridization assays may be repeated on a regular basis to evaluate whether the level of expression in the patient begins to approximate that which is observed in the normal patient. The results obtained from successive assays may be used to show the efficacy of treatment over a period ranging from several days to months.

With respect to cancer, the presence of a relatively high amount of transcript in biopsied tissue from an individual may indicate a predisposition for the development of the disease, or may provide a means for detecting the disease prior to the appearance of actual clinical symptoms. A more definitive diagnosis of this type may allow health professionals to employ preventative measures or aggressive treatment earlier thereby preventing the development or further progression of the cancer.

Additional diagnostic uses for oligonucleotides designed from the sequences encoding RABP may involve the use of PCR. Such oligomers may be chemically synthesized, generated enzymatically, or produced in vitro. Oligomers will preferably consist of two nucleotide sequences, one with sense orientation (5'→3') and another with antisense (3'←5'), employed under optimized conditions for identification of a specific gene or condition. The same two oligomers, nested sets of oligomers, or even a degenerate pool of oligomers may be employed under less stringent conditions for detection and/or quantitation of closely related DNA or RNA sequences.

Methods which may also be used to quantitate the expression of RABP include radiolabeling or biotinylating nucleotides, coamplification of a control nucleic acid, and standard curves onto which the experimental results are interpolated (Melby, P. C. et al. (1993) J. Immunol. Methods, 159:235–244; Duplaa, C. et al. (1993) Anal. Biochem. 229–236). The speed of quantitation of multiple samples may be accelerated by running the assay in an ELISA format where the oligomer of interest is presented in various dilutions and a spectrophotometric or colorimetric response gives rapid quantitation.

In further embodiments, an oligonucleotide derived from any of the polynucleotide sequences described herein may be used as a target in a microarray. The microarray can be used to monitor the expression level of large numbers of genes simultaneously (to produce a transcript image), and to identify genetic variants, mutations and polymorphisms. This information will be useful in determining gene function, understanding the genetic basis of disease, diagnosing disease, and in developing and monitoring the activity of therapeutic agents (Heller, R. et al. (1997) Proc. Natl. Acad. Sci. 94:2150–55).

In one embodiment, the microarray is prepared and used according to the methods described in PCT application WO95/11995 (Chee et al.), Lockhart, D. J. et al. (1996; Nat. Biotech. 14: 1675–1680) and Schena, M. et al. (1996; Proc. Natl. Acad. Sci. 93: 10614–10619), all of which are incorporated herein in their entirety by reference.

The microarray is preferably composed of a large number of unique, single-stranded nucleic acid sequences, usually either synthetic antisense oligonucleotides or fragments of cDNAs, fixed to a solid support. The oligonucleotides are preferably about 6–60 nucleotides in length, more preferably 15–30 nucleotides in length, and most preferably about 20–25 nucleotides in length. For a certain type of microarray, it may be preferable to use oligonucleotides which are only 7–10 nucleotides in length. The microarray may contain oligonucleotides which cover the known 5', or 3', sequence, sequential oligonucleotides which cover the full length sequence; or unique oligonucleotides selected from particular areas along the length of the sequence. Polynucleotides used in the microarray may be oligonucleotides that are specific to a gene or genes of interest in which at least a fragment of the sequence is known or that are specific to one or more unidentified cDNAs which are common to a particular cell type, developmental or disease state.

In order to produce oligonucleotides to a known sequence for a microarray, the gene of interest is examined using a computer algorithm which starts at the 5' or more preferably at the 3' end of the nucleotide sequence. The algorithm identifies oligomers of defined length that are unique to the gene, have a GC content within a range suitable for hybridization, and lack predicted secondary structure that may interfere with hybridization. In certain situations it may be appropriate to use pairs of oligonucleotides on a microarray. The "pairs" will be identical, except for one nucleotide which preferably is located in the center of the sequence. The second oligonucleotide in the pair (mismatched by one) serves as a control. The number of oligonucleotide pairs may range from two to one million. The oligomers are synthesized at designated areas on a substrate using a light-directed chemical process. The substrate may be paper, nylon or other type of membrane, filter, chip, glass slide or any other suitable solid support.

In another aspect, an oligonucleotide may be synthesized on the surface of the substrate by using a chemical coupling procedure and an ink jet application apparatus, as described in PCT application WO95/251116 (Baldeschweiler et al.) which is incorporated herein in its entirety by reference. In another aspect, a "gridded" array analogous to a dot (or slot) blot may be used to arrange and link cDNA fragments or oligonucleotides to the surface of a substrate using a vacuum system, thermal, UV, mechanical or chemical bonding procedures. An array, such as those described above, may be produced by hand or by using available devices (slot blot or dot blot apparatus), materials (any suitable solid support), and machines (including robotic instruments), and may contain 8, 24, 96, 384, 1536 or 6144 oligonucleotides, or any other number between two and one million which lends itself to the efficient use of commercially available instrumentation.

In order to conduct sample analysis using a microarray, the RNA or DNA from a biological sample is made into hybridization probes. The mRNA is isolated, and cDNA is produced and used as a template to make antisense RNA (aDNA). The aRNA is amplified in the presence of fluorescent nucleotides, and labeled probes are incubated with the microarray so that the probe sequences hybridize to complementary oligonucleotides of the microarray. Incubation conditions are adjusted so that hybridization occurs with precise complementary matches or with various degrees of less complementarity. After removal of nonhybridized probes, a scanner is used to determine the levels and patterns of fluorescence. The scanned images are examined to determine degree of complementarity and the relative abundance of each oligonucleotide sequence on the microarray. The biological samples may be obtained from any bodily fluids (such as blood, urine, saliva, phlegm, gastric juices, etc.), cultured cells, biopsies, or other tissue preparations. A detection system may be used to measure the absence, presence, and amount of hybridization for all of the distinct sequences simultaneously. This data may be used for large scale correlation studies on the sequences, mutations, variants, or polymorphisms among samples.

In another embodiment of the invention, the nucleic acid sequences which encode RABP may also be used to generate hybridization probes which are useful for mapping the naturally occurring genomic sequence. The sequences may be mapped to a particular chromosome, to a specific region of a chromosome or to artificial chromosome constructions, such as human artificial chromosomes (HACs), yeast artificial chromosomes (YACs), bacterial artificial chromosomes (BACs), bacterial P1 constructions or single chromosome cDNA libraries as reviewed in Price, C. M. (1993) Blood Rev. 7:127–134, and Trask, B. J. (1991) Trends Genet. 7:149–154.

Fluorescent in situ hybridization (FISH as described in Verma et al. (1988) *Human Chromosomes: A Manual of Basic Techniques*, Pergamon Press, New York, N.Y.) may be correlated with other physical chromosome mapping techniques and genetic map data. Examples of genetic map data can be found in various scientific journals or at Online Mendelian Inheritance in Man (OMIM). Correlation between the location of the gene encoding RABP on a physical chromosomal map and a specific disease, or predisposition to a specific disease, may help delimit the region of DNA associated with that genetic disease. The nucleotide sequences of the subject invention may be used to detect differences in gene sequences between normal, carrier, or affected individuals.

In situ hybridization of chromosomal preparations and physical mapping techniques such as linkage analysis using established chromosomal markers may be used for extending genetic maps. Often the placement of a gene on the chromosome of another mammalian species, such as mouse, may reveal associated markers even if the number or arm of a particular human chromosome is not known. New sequences can be assigned to chromosomal arms, or parts thereof, by physical mapping. This provides valuable information to investigators searching for disease genes using positional cloning or other gene discovery techniques. Once the disease or syndrome has been crudely localized by genetic linkage to a particular genomic region, for example, AT to 11q22–23 (Gatti, R. A. et al. (1988) Nature 336:577–580), any sequences mapping to that area may represent associated or regulatory genes for further investigation. The nucleotide sequence of the subject invention may also be used to detect differences in the chromosomal location due to translocation, inversion, etc. among normal, carrier, or affected individuals.

In another embodiment of the invention, RABP, its catalytic or immunogenic fragments or oligopeptides thereof, can be used for screening libraries of compounds in any of a variety of drug screening techniques. The fragment employed in such screening may be free in solution, affixed to a solid support, borne on a cell surface, or located intracellularly. The formation of binding complexes, between RABP and the agent being tested, may be measured.

Another technique for drug screening which may be used provides for high throughput screening of compounds having suitable binding affinity to the protein of interest as described in published PCT application WO84/03564. In this method, as applied to RABP, large numbers of different small test compounds are synthesized on a solid substrate, such as plastic pins or some other surface. The test compounds are reacted with RABP, or fragments thereof, and washed. Bound RABP is then detected by methods well known in the art. Purified RABP can also be coated directly onto plates for use in the aforementioned drug screening techniques. Alternatively, non-neutralizing antibodies can be used to capture the peptide and immobilize it on a solid support.

In another embodiment, one may use competitive drug screening assays in which neutralizing antibodies capable of binding RABP specifically compete with a test compound for binding RABP. In this manner, the antibodies can be used to detect the presence of any peptide which shares one or more antigenic determinants with RABP.

In additional embodiments, the nucleotide sequences which encode RABP may be used in any molecular biology techniques that have yet to be developed, provided the new techniques rely on properties of nucleotide sequences that are currently known, including, but not limited to, such properties as the triplet genetic code and specific base pair interactions.

The examples below are provided to illustrate the subject invention and are not included for the purpose of limiting the invention.

EXAMPLES

I cDNA Library Construction

The NGANNOT01 cDNA library was constructed using 1 microgram of polyA RNA isolated from tumorous neuroganglion tissue removed from a 9-year-old Caucasian male during a soft tissue excision of the chest wall. Pathology indicated a ganglioneuroma forming an encapsulated lobulated mass. Examination of the medial aspect of the pleura surrounding the tumor showed fibrotic tissue with chronic inflammation that extended into the overlying adipose tissue. The patient presented with a cough and was not taking any medications.

The LIVRTUT04 cDNA library was constructed using 7.5 nanograms of polyA RNA isolated from liver tumor tissue removed from a 50-year-old Caucasian male during a partial hepatectomy. Pathology indicated a grade 3–4 hepatoma; surgical margins free of tumor; and no lymphovascular invasion. The adjacent liver showed mild portal fibrosis with lymphoid aggregates and mild steatosis. Patient history included benign hypertension and hepatitis.

The UTRSNOT16 cDNA library was constructed using 2 micrograms of polyA RNA isolated from nontumorous uterine endometrial tissue removed from a 48-year-old Caucasian female during a vaginal hysterectomy, rectocele repair, and bilateral salpingo-oopherectomy. Pathology indicated chronic cervicitis, and the endometrium was weakly proliferative. The uterus, tubes, ovaries, and specimen from the peritoneum indicated endometriosis focally involving the surface of the right ovary and the peritoneum. Pathology for the associated tumor tissue indicated a single submucosal leiomyoma, which exhibited extensive hyalin change with hyalin-type necrosis. The left ovary contained a corpus luteum cyst, and the right and left fallopian tubes were unremarkable. The patient presented with metrorrhagia, extrinsic asthma, depressive disorder, and anxiety.

The frozen tissues were homogenized and lysed using a Brinkmann Homogenizer Polytron PT-3000 (Brinkmann Instruments, Westbury, N.J.) in guanidinium isothiocyanate solution. The lysates were centrifuged over a 5.7 M CsCl cushion using a Beckman SW28 rotor in a Beckman L8–70M Ultracentrifuge (Beckman Instruments) for 18 hours at 25,000 rpm at ambient temperature. The RNA was extracted with acid phenol pH 4.7, precipitated using 0.3 M sodium acetate and 2.5 volumes of ethanol, resuspended in RNAse-free water, and DNase treated at 37° C. RNA extraction and precipitation were repeated as before. The MRNA was then isolated using the Qiagen OLIGOTEX kit (QIAGEN, Chatsworth, Calif.) and used to construct the cDNA libraries.

The mRNAs were handled according to the recommended protocols in the SuperScript Plasmid System for cDNA Synthesis and Plasmid Cloning (Cat. #18248-013, Gibco/BRL). cDNAs were fractionated on a SEPAHROSE CL4B column (Cat. #275105-01, Pharmacia), and those cDNAs exceeding 400 bp were ligated into PSPORT 1 (NGANNOT01) or pINCY (LIVRTUT04 and UTRSNOT16). The plasmid PSPORT 1 or pINCY were subsequently transformed into DH5α competent cells (Cat. #18258-012, Gibco/BRL).

II Isolation and Sequencing of cDNA Clones

Plasmid DNA was released from the cells and purified using the REAL Prep 96 Plasmid Kit (Catalog #26173, QIAGEN). This kit enabled the simultaneous purification of 96 samples in a 96-well block using multi-channel reagent dispensers. The recommended protocol was employed except for the following changes: 1) the bacteria were cultured in 1 ml of sterile Terrific Broth (Catalog #22711, GIBCO/BRL) with carbenicillin at 25 mg/L and glycerol at 0.4%; 2) after inoculation, the cultures were incubated for 19 hours and at the end of incubation, the cells were lysed with 0.3 ml of lysis buffer; and 3) following isopropanol precipitation, the plasmid DNA pellet was resuspended in 0.1 ml of distilled water. After the last step in the protocol, samples were transferred to a 96-well block for storage at 4° C.

The cDNAs were sequenced by the method of Sanger et al. (1975, J. Mol. Biol. 94:441f), using a Hamilton Micro Lab 2200 (Hamilton, Reno, Nev.) in combination with Peltier Thermal Cyclers (PTC200 from MJ Research, Watertown, Mass.) and Applied Biosystems 377 DNA Sequencing Systems; and the reading frame was determined.

III Homology Searching of cDNA Clones and Their Deduced Proteins

The nucleotide sequences of the Sequence Listing or amino acid sequences deduced from them were used as query sequences against databases such as GenBank, SwissProt, BLOCKS, and Pima II. These databases which contain previously identified and annotated sequences were searched for regions of homology (similarity) using BLAST, which stands for Basic Local Alignment Search Tool (Altschul SF (1993) J. Mol. Evol. 36:290–300; Altschul, S F et al. (1990) J. Mol. Biol. 215:403–10).

BLAST produces alignments of both nucleotide and amino acid sequences to determine sequence similarity. Because of the local nature of the alignments, BLAST is especially useful in determining exact matches or in identifying homologs which may be of prokaryotic (bacterial) or eukaryotic (animal, fungal or plant) origin. Other algorithms such as the one described in Smith R F and T F Smith (1992 Protein Engineering 5:35–51), incorporated herein by reference, can be used when dealing with primary sequence patterns and secondary structure gap penalties. As disclosed in this application, the sequences have lengths of at least 49 nucleotides, and no more than 12% uncalled bases (where N is recorded rather than A, C, G, or T).

The BLAST approach, as detailed in Karlin and Altschul (1993; Proc Nat Acad Sci 90:5873–7) and incorporated herein by reference, searches matches between a query sequence and a database sequence, to evaluate the statistical significance of any matches found, and to report only those matches which satisfy the user-selected threshold of significance. In this application, threshold was set at 10–25 for nucleotides and 10–14 for peptides.

IV Northern Analysis

Northern analysis is a laboratory technique used to detect the presence of a transcript of a gene and involves the hybridization of a labeled nucleotide sequence to a membrane on which RNAs from a particular cell type or tissue have been bound (Sambrook et al., supra).

Analogous computer techniques using BLAST (Altschul, S. F. (1993) J. Mol. Evol. 36:290–300; Altschul, S. F. et al. (1990) J. Mol. Evol. 215:403–410) are used to search for identical or related molecules in nucleotide databases such as GenBank or the LIFESEQ database (Incyte Pharmaceuticals). This analysis is much faster than multiple, membrane-based hybridizations. In addition, the sensitivity of the computer search can be modified to determine whether any particular match is categorized as exact or homologous.

The basis of the search is the product score which is defined as:

$$\frac{\% \text{ sequence identity} \times \% \text{ maximum BLAST score}}{100}$$

The product score takes into account both the degree of similarity between two sequences and the length of the sequence match. For example, with a product score of 40, the match will be exact within a 1–2% error; and at 70, the match will be exact. Homologous molecules are usually identified by selecting those which show product scores between 15 and 40, although lower scores may identify related molecules.

The results of northern analysis are reported as a list of libraries in which the transcript encoding RABP occurs. Abundance and percent abundance are also reported. Abundance directly reflects the number of times a particular transcript is represented in a cDNA library, and percent abundance is abundance divided by the total number of sequences examined in the cDNA library.

V Extension of RABP Encoding Polynucleotides

The nucleic acid sequence of the Incyte Clone 2312652, 2514506, or 3400003 was used to design oligonucleotide primers for extending a partial nucleotide sequence to full length. One primer was synthesized to initiate extension in the antisense direction, and the other was synthesized to extend sequence in the sense direction. Primers were used to facilitate the extension of the known sequence "outward" generating amplicons containing new, unknown nucleotide sequence for the region of interest. The initial primers were designed from the cDNA using OLIGO 4.06 (National Biosciences), or another appropriate program, to be about 22 to about 30 nucleotides in length, to have a GC content of 50% or more, and to anneal to the target sequence at temperatures of about 68° to about 72° C. Any stretch of nucleotides which would result in hairpin structures and primer-primer dimerizations was avoided.

Selected human cDNA libraries (Gibco/BRL) were used to extend the sequence. If more than one extension is necessary or desired, additional sets of primers are designed to further extend the known region.

High fidelity amplification was obtained by following the instructions for the XL-PCR kit (Perkin Elmer) and thoroughly mixing the enzyme and reaction mix. Beginning with 40 pmol of each primer and the recommended concentrations of all other components of the kit, PCR was performed using the Peltier Thermal Cycler (PTC200; M. J. Research, Watertown, Mass.) and the following parameters:

Step 1 94° C. for 1 min (initial denaturation)
Step 2 65° C. for 1 min
Step 3 68° C. for 6 min
Step 4 94° C. for 15 sec
Step 5 65° C. for 1 min
Step 6 68° C. for 7 min
Step 7 Repeat step 4–6 for 15 additional cycles
Step 8 94° C. for 15 sec
Step 9 65° C. for 1 min
Step 10 68° C. for 7:15 min
Step 11 Repeat step 8–10 for 12 cycles
Step 12 72° C. for 8 min
Step 13° C. (and holding)

A 5–10 µl aliquot of the reaction mixture was analyzed by electrophoresis on a low concentration (about 0.6–0.8%) agarose mini-gel to determine which reactions were successful in extending the sequence. Bands thought to contain the largest products were excised from the gel, purified using QIAQuick™ (QIAGEN Inc., Chatsworth, Calif.), and trimmed of overhangs using Klenow enzyme to facilitate religation and cloning.

After ethanol precipitation, the products were redissolved in 13 µl of ligation buffer, 1 µl T4-DNA ligase (15 units) and 1 µl T4 polynucleotide kinase were added, and the mixture was incubated at room temperature for 2–3 hours or overnight at 16° C. Competent *E. coli* cells (in 40 µl of appropriate media) were transformed with 3 µl of ligation mixture and cultured in 80 µl of SOC medium (Sambrook et al., supra). After incubation for one hour at 37° C., the *E. coli* mixture was plated on Luria Bertani (LB)-agar (Sambrook et al., supra) containing 2× Carb. The following day, several colonies were randomly picked from each plate and cultured in 150 µl of liquid LB/2× Carb medium placed in an individual well of an appropriate, commercially-available, sterile 96-well microtiter plate. The following day, 5 µl of each overnight culture was transferred into a non-sterile 96-well plate and after dilution 1:0 with water, 5 µl of each sample was transferred into a PCR array.

For PCR amplification, 18 µl of concentrated PCR reaction mix (3.3×) containing 4 units of rTth DNA polymerase, a vector primer, and one or both of the gene specific primers used for the extension reaction were added to each well. Amplification was performed using the following conditions:

Step 1 94° C. for 60 sec
Step 2 94° C. for 20 sec
Step 3 55° C. for 30 sec
Step 4 72° C. for 90 sec
Step 5 Repeat steps 2–4 for an additional 29 cycles
Step 6 72° C. for 180 sec
Step 7 4° C. (and holding)

Aliquots of the PCR reactions were run on agarose gels together with molecular weight markers. The sizes of the PCR products were compared to the original partial cDNAs, and appropriate clones were selected, ligated into plasmid, and sequenced.

In like manner, the nucleotide sequence of SEQ ID NO:2, SEQ ID NO:4, or SEQ ID NO:6, is used to obtain 5' regulatory sequences using the procedure above, oligonucleotides designed for 5' extension, and an appropriate genomic library.

VI Labeling and Use of Individual Hybridization Probes

Hybridization probes derived from SEQ ID NO:2, SEQ ID NO:4, or SEQ ID NO:6 are employed to screen cDNAs, genomic DNAs, or mRNAs. Although the labeling of oligonucleotides, consisting of about 20 base-pairs, is specifically described, essentially the same procedure is used with larger nucleotide fragments. Oligonucleotides are designed using state-of-the-art software such as OLIGO 4.06 (National Biosciences), labeled by combining 50 pmol of each oligomer and 250 µCi of [$\gamma$-$^{32}$P] adenosine triphosphate (Amersham) and T4 polynucleotide kinase (DuPont NEN, Boston, Mass.). The labeled oligonucleotides are substantially purified with SEPHADEX G-25 superfine resin column (Pharmacia & Upjohn). A aliquot containing $10^7$ counts per minute of the labeled probe is used in a typical membrane-based hybridization analysis of human genomic DNA digested with one of the following endonucleases (Ase I, Bgl II, Eco RI, Pst I, Xba 1, or Pvu II; DuPont NEN).

The DNA from each digest is fractionated on a 0.7 percent agarose gel and transferred to nylon membranes (Nytran Plus, Schleicher & Schuell, Durham, N.H.). Hybridization is carried out for 16 hours at 40° C. To remove nonspecific signals, blots are sequentially washed at room temperature under increasingly stringent conditions up to 0.1× saline sodium citrate and 0.5% sodium dodecyl sulfate. After XOMAT AR film (Kodak, Rochester, N.Y.) is exposed to the blots in a Phosphoimager cassette (Molecular Dynamics, Sunnyvale, Calif.) for several hours, hybridization patterns are compared visually.

VII Microarrays

To produce oligonucleotides for a microarray, the nucleotide sequence described herein is examined using a computer algorithm which starts at the 3' end of the nucleotide sequence. The algorithm identifies oligomers of defined length that are unique to the gene, have a GC content within a range suitable for hybridization, and lack predicted secondary structure that would interfere with hybridization. The algorithm identifies 20 sequence-specific oligonucleotides of 20 nucleotides in length (20-mers). A matched set of oligonucleotides is created in which one nucleotide in the center of each sequence is altered. This process is repeated for each gene in the microarray, and double sets of twenty 20 mers are synthesized and arranged on the surface of the silicon chip using a light-directed chemical process (Chee, M. et al., PCT/WO95/11995, incorporated herein by reference).

In the alternative, a chemical coupling procedure and an ink jet device are used to synthesize oligomers on the surface of a substrate (Baldeschweiler, J. D. et al., PCT/WO95/25116, incorporated herein by reference). In another alternative, a "gridded" array analogous to a dot (or slot) blot is used to arrange and link cDNA fragments or oligonucleotides to the surface of a substrate using a vacuum system, thermal, UV, mechanical or chemical bonding procedures. An array may be produced by hand or using available materials and machines and contain grids of 8 dots, 24 dots, 96 dots, 384 dots, 1536 dots or 6144 dots. After hybridization, the microarray is washed to remove nonhybridized probes and a scanner is used to determine the levels and patterns of fluorescence. The scanned images are examined to determine degree of complementarity and the relative abundance of each oligonucleotide sequence on the micro-array.

VIII Complementary Polynucleotides

Sequence complementary to the RABP-encoding sequence, or any part thereof, is used to decrease or inhibit expression of naturally occurring RABP. Although use of oligonucleotides comprising from about 15 to about 30 base-pairs is described, essentially the same procedure is used with smaller or larger sequence fragments. Appropriate oligonucleotides are designed using Oligo 4.06 software and the coding sequence of RABP, SEQ ID NO:1, SEQ ID NO:3, or SEQ ID NO:5. To inhibit transcription, a complementary oligonucleotide is designed from the most unique 5' sequence and used to prevent promoter binding to the coding sequence. To inhibit translation, a complementary oligonucleotide is designed to prevent ribosomal binding to the RABP-encoding transcript.

IX Expression of RABP

Expression of RABP is accomplished by subcloning the cDNAs into appropriate vectors and transforming the vectors into host cells. In this case, the cloning vector is also used to express RABP in *E. coli*. Upstream of the cloning site, this vector contains a promoter for β-galactosidase, followed by sequence containing the amino-terminal Met, and the subsequent seven residues of β-galactosidase. Immediately following these eight residues is a bacteriophage promoter useful for transcription and a linker containing a number of unique restriction sites.

Induction of an isolated, transformed bacterial strain with IPTG using standard methods produces a fusion protein which consists of the first eight residues of β-galactosidase, about 5 to 15 residues of linker, and the full length protein. The signal residues direct the secretion of RABP into the bacterial growth media which can be used directly in the following assay for activity.

X Demonstration of RABP Activity

RABP can be expressed in a mammalian cell line such as 293T by transfecting with an eukaryotic expression vector encoding RABP. Eukaryotic expression vectors are commercially available, and the techniques to introduce them into cells are well known to those skilled in the art. A small amount of a second plasmid, which expresses any one of a number of reporter genes such as β-galactosidase, is co-transformed into the cells in order to allow rapid identification of those cells which have taken up and expressed the foreign DNA. The cells are cultured in a defined synthetic medium with concentrations of GTP for at least 48 hours after transformation to allow expression and accumulation of RABP and β-galactosidase.

Transformed cells expressing β-galactosidase are stained blue when a suitable colorimetric substrate is added to the culture media under conditions that are well known in the art. Increasing concentrations of GTP induces increasing numbers of reporter gene positive cells (Ren, M. et al. (1996) Proc. Natl. Acad. Sci. 93: 5151–5155). GTP-treated cells which were no t transformed with the RABP expression vector are used as controls as are RABP transfected cells cultured without supplemental GTP.

XI Production of RABP Specific Antibodies

RABP that is substantially purified using PAGE electrophoresis (Sambrook, supra), or other purification techniques, is used to immunize rabbits and to produce antibodies using standard protocols. The amino acid sequence deduced from SEQ ID NO:2, SEQ ID NO:4, or SEQ ID NO:6 is analyzed using DNASTAR software (DNASTAR Inc) to determine regions of high immunogenicity and a corresponding oligopeptide is synthesized and used to raise antibodies by means known to those of skill in the art. Selection of appropriate epitopes, such as those near the C-terminus or in hydrophilic regions, is described by Ausubel et al. (supra), and others.

Typically, the oligopeptides are 15 residues in length, synthesized using an Applied Biosystems Peptide Synthesizer Model 431A using fmoc-chemistry, and coupled to keyhole limpet hemocyanin (KLH, Sigma, St. Louis, Mo.) by reaction with N-maleimidobenzoyl-N-hydroxysuccinimide ester (MBS; Ausubel et al., supra). Rabbits are immunized with the oligopeptide-KLH complex in complete Freund's adjuvant. The resulting antisera are tested for antipeptide activity, for example, by binding the peptide to plastic, blocking with 1% BSA, reacting with rabbit antisera, washing, and reacting with radio iodinated, goat anti-rabbit IgG.

XII Purification of Naturally Occurring RABP Using Specific Antibodies

Naturally occurring or recombinant RABP is substantially purified by immunoaffinity chromatography using antibodies specific for RABP. An immunoaffinity column is constructed by covalently coupling RABP antibody to an activated chromatographic resin, such as CNBr-activated SEPHAROSE (Pharmacia & Upjohn). After the coupling, the resin is blocked and washed according to the manufacturer's instructions.

Media containing RABP is passed over the immunoaffinity column, and the column is washed under conditions that allow the preferential absorbance of RABP (e.g., high ionic strength buffers in the presence of detergent). The column is eluted under conditions that disrupt antibody/RABP binding (eg, a buffer of pH 2–3 or a high concentration of a chaotrope, such as urea or thiocyanate ion), and RABP is collected.

XIII Identification of Molecules Which Interact with RABP

RABP or biologically active fragments thereof are labeled with $^{125}$I Bolton-Hunter reagent (Bolton et al. (1973) Biochem. J. 133: 529). Candidate molecules previously arrayed in the wells of a multi-well plate are incubated with the labeled RABP, washed and any wells with labeled RABP complex are assayed. Data obtained using different concentrations of RABP are used to calculate values for the number, affinity, and association of RABP with the candidate molecules.

All publications and patents mentioned in the above specification are herein incorporated by reference. Various modifications and variations of the described method and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are obvious to those skilled in molecular biology or related fields are intended to be within the scope of the following claims.

What is claimed is:

1. A substantially purified polypeptide comprising an amino acid sequence selected from the group consisting of
   a) an amino acid sequence of SEQ ID NO:1,
   b) a amino acid sequence having at least 90% sequence identity to the sequence of SEQ ID NO:1 wherein said sequence possess GTP binding activity,
   c) a biologically-active fragment of the amino acid sequence of SEQ ID NO:1, wherein said biologically-active fragment possesses GTP binding activity, and
   d) an antigenically-active fragment of the amino acid sequence of SEQ ID NO:1 wherein said immunologically active fragment generates an antibody that specifically binds to the polypeptide encoded by SEQ ID NO:1.

2. A composition comprising a polypeptide of claim 1 in conjunction with a suitable pharmaceutical carrier.

3. A purified antibody which specifically binds to a polypeptide of claim 1.

4. A method for stimulating cell proliferation comprising administering to a cell an effective amount of the composition of claim 3.

5. A polypeptide of claim 1, having the amino acid sequence of SEQ ID NO:1.

6. A composition comprising a polypeptide of claim 5 in conjunction with a suitable pharmaceutical carrier.

* * * * *

SEQUENCE LISTING (1) GENERAL INFORMATION:

(iii) NUMBER OF SEQUENCES: 9

(2) INFORMATION FOR SEQ ID NO:1:

(i) SEQUENCE CHARACTERISTICS:
      (A) LENGTH: 203 amino acids
      (B) TYPE: amino acid
      (C) STRANDEDNESS: single
      (D) TOPOLOGY: linear (vii) IMMEDIATE SOURCE:
      (A) LIBRARY: NGANNOT01
      (B) CLONE: 2312652

(xi) SEQUENCE DESCRIPTION: SEQ ID NO:1:

```
Met Ser Gly Gln Arg Val Asp Val Lys Val Met Leu Gly Lys Glu
 1               5                  10                  15

Tyr Val Gly Lys Thr Ser Leu Val Glu Arg Tyr Val His Xaa Xaa Phe
                20                  25                  30

Leu Val Gly Pro Tyr Gln Asn Thr Ile Gly Ala Ala Phe Val Ala Lys
                35                  40                  45

Val Met Ser Val Gly Asp Arg Thr Val Thr Leu Gly Ile Trp Asp Thr
 50                  55                  60

Ala Gly Ser Glu Arg Tyr Glu Ala Met Ser Arg Ile Tyr Tyr Arg Gly
 65                  70                  75                  80

Ala Lys Ala Ala Ile Val Cys Tyr Asp Leu Thr Asp Ser Ser Ser Phe
                85                  90                  95

Glu Arg Ala Lys Phe Trp Val Lys Glu Leu Arg Ser Leu Glu Glu Gly
                100                 105                 110

Cys Gln Ile Tyr Leu Cys Gly Thr Lys Ser Asp Leu Leu Glu Glu Asp
                115                 120                 125

Arg Arg Arg Arg Arg Val Asp Phe His Asp Val Gln Asp Tyr Ala Asp
 130                 135                 140

Asn Ile Lys Ala Gln Leu Phe Glu Thr Ser Ser Lys Thr Gly Gln Ser
145                 150                 155                 160

Val Asp Glu Leu Phe Gln Lys Val Ala Glu Asp Tyr Val Ser Val Ala
                165                 170                 175

Ala Phe Gln Val Met Thr Glu Asp Lys Gly Val Asp Leu Gly Gln Lys
                180                 185                 190

Pro Asn Pro Tyr Phe Tyr Ser Cys Cys His His
                195                 200
```

(2) INFORMATION FOR SEQ ID NO:2:

(i) SEQUENCE CHARACTERISTICS:
      (A) LENGTH: 1334 base pairs
      (B) TYPE: nucleic acid
      (C) STRANDEDNESS: single
      (D) TOPOLOGY: linear (vii) IMMEDIATE SOURCE:
      (A) LIBRARY: NGANNOT01
      (B) CLONE: 2312652

(xi) SEQUENCE DESCRIPTION: SEQ ID NO:2:

```
CCCACGCGTC CGCGCGGCGC TGCGGGTAGG AGCCGGGTTG CGGGAGACCC CAGGTTCGGT     60

TGGGATTCCC AGCCAGAACG GAGCTTAAGC CGGGCAGGCG AGCGAATGAC GGAGTAGCGA    120
```

-continued

```
GCTGCACGGC GGCGTGCTGC GCTGTTGAGG ACGCTGTCCC GCGCGCTCCC AGGCCGCCCC      180

GAGGCTTGGG GTCTTCGAAG GATAATCGGC GCCCGGGGCC GAACAGCGGG GGCACACGGG      240

GCGCTGCCGA AGTGCAAGGC CACGGCCAGA GCTCGAGCCC GACGCGCTGT CTGGAGTCGT      300

AGGTTGGCGC CGTTTGGGGT CGGGGTCTGA GGCTTGGGCG CTGCCTGGGC CGAGCGGAGA      360

TCGGGGTTTG CCTCCCGTCC CCGCTCAGGA CCCTGACGTG GCTGAAGCGG CCCCGGGAGC      420

ATGAGCGGGC AGCGCGTGGA CGTCAAGGTG GTGATGCTGG GCAAGGAGTA CGTGGGCAAG      480

ACTAGCCTGG TGGAGCGCTA CGTGCACGNC NGCTTTCTGG TGGGGCCTTA TCAGAACACC      540

ATCGGGGCCG CGTTCGTGGC CAAGGTGATG TCGGTCGGAG ACCGGACTGT GACATTAGGT      600

ATTTGGGACA CAGCAGGCTC TGAGCGCTAT GAGGCCATGA GTAGAATCTA CTATCGGGGT      660

GCCAAGGCTG CCATCGTCTG CTATGACCTC ACAGACAGCA GCAGCTTTGA GCGAGCAAAG      720

TTCTGGGTGA AGGAACTGCG CAGCCTAGAG GAGGGCTGCC AAATCTACTT ATGTGGCACC      780

AAGAGTGACC TGCTGGAAGA AGACCGGAGG CGTCGACGTG TGGACTTCCA CGACGTCCAG      840

GACTATCAG ACAATATCAA AGCTCAGCTC TTTGAAACAT CCAGCAAGAC AGGCCAGAGT      900

GTGGACGAGC TCTTCCAGAA AGTGGCAGAG GATTACGTCA GTGTGGCTGC CTTCCAGGTG      960

ATGACAGAGG ACAAGGGCGT GGATCTGGGC CAGAAGCCAA ACCCTACTT CTACAGCTGT     1020

TGTCATCACT GAGTCAGCAC TCACCTGGCC TGGGGGAATT AAAGGAATTC CCCGTAAGGG     1080

CTGGACCCAG CTCCTTTCTG GGCTTGGGTA GTCAAATGTC TGAGCTACCC CAGGTCCTCA     1140

TGTCAGCAGA GTGGCGCCTG CCTGTGCTGG CCCATGGAAC GGAGACAGCA TTGGGCTGAC     1200

TGTGGGCATG AGGAGGGATA AGGCTGATTT GGACCCCAGG CTTCTGCCCT GGACAGCACT     1260

TGTGTCTGCA GATTATTTAA GTGGCTTTTG ATCTGTAAAT AAAATCAGTG CACTGTGAAT     1320

CACAAAAAAA AAGG                                                      1334
```

(2) INFORMATION FOR SEQ ID NO:3:

(i) SEQUENCE CHARACTERISTICS:
        (A) LENGTH: 201 amino acids
        (B) TYPE: amino acid
        (C) STRANDEDNESS: single
        (D) TOPOLOGY: linear (vii) IMMEDIATE SOURCE:
        (A) LIBRARY: LIVRTUT04
        (B) CLONE: 2514506

(xi) SEQUENCE DESCRIPTION: SEQ ID NO:3:

```
Met Asn Pro Glu Tyr Asp Tyr Leu Phe Lys Leu Leu Ile Gly Asp
 1               5                  10                  15

Ser Gly Val Gly Lys Ser Cys Leu Leu Leu Arg Phe Ala Asp Thr
                20                  25                  30

Tyr Thr Glu Ser Tyr Ile Ser Thr Ile Gly Val Asp Phe Lys Ile Arg
            35                  40                  45

Thr Ile Glu Leu Asp Gly Lys Thr Ile Lys Leu Gln Ile Trp Asp Thr
        50                  55                  60

Ala Gly Gln Glu Arg Phe Arg Thr Ile Thr Ser Ser Tyr Tyr Arg Gly
65                  70                  75                  80

Ala His Gly Ile Ile Val Val Tyr Asp Val Thr Asp Gln Glu Ser Tyr
                85                  90                  95

Ala Asn Val Lys Gln Trp Leu Gln Glu Ile Asp Arg Tyr Ala Ser Glu
               100                 105                 110
```

```
Asn Val Asn Lys Leu Leu Val Gly Asn Lys Ser Asp Leu Thr Thr Lys
        115                 120                 125

Lys Val Val Asp Asn Thr Thr Ala Lys Glu Phe Ala Asp Ser Leu Gly
    130                 135                 140

Ile Pro Phe Leu Glu Thr Ser Ala Lys Asn Ala Thr Asn Val Glu Gln
145                 150                 155                 160

Ala Phe Met Thr Met Ala Ala Glu Ile Lys Lys Arg Met Gly Pro Gly
                165                 170                 175

Ala Ala Ser Gly Gly Glu Arg Pro Asn Leu Lys Ile Asp Ser Thr Pro
            180                 185                 190

Val Lys Pro Ala Gly Gly Gly Cys Cys
        195                 200
```

(2) INFORMATION FOR SEQ ID NO:4:

(i) SEQUENCE CHARACTERISTICS:
        (A) LENGTH: 925 base pairs
        (B) TYPE: nucleic acid
        (C) STRANDEDNESS: single
        (D) TOPOLOGY: linear (vii) IMMEDIATE SOURCE:
        (A) LIBRARY: LIVRTUT04
        (B) CLONE: 2514506

(xi) SEQUENCE DESCRIPTION: SEQ ID NO:4:

```
ACCATCTTGG AACGGGAGGC GGACAGAGTC GACTGGGAGC GACCGAGCGG GCCGCCGCCG      60

CCGCCATGAA CCCCGAATAT GACTACCTGT TTAAGCTGCT TTTGATTGGC GACTCAGGCG     120

TGGGCAAGTC ATGCCTGCTC CTGCGGTTTG CTGATGACAC GTACACAGAG AGCTACATCA     180

GCACCATCGG GGTGGACTTC AAGATCCGAA CCATCGAGCT GGATGGCAAA ACTATCAAAC     240

TTCAGATCTG GGACACAGCG GGCCAGGAAC GGTTCCGGAC CATCACTTCC AGCTACTACC     300

GGGGGGCTCA TGGCATCATC GTGGTGTATG ACGTCACTGA CCAGGAATCC TACGCCAACG     360

TGAAGCAGTG GCTGCAGGAG ATTGACCGCT ATGCCAGCGA GAACGTCAAT AAGCTCCTGG     420

TGGGCAACAA GAGCGACCTC ACCACCAAGA AGGTGGTGGA CAACACCACA GCCAAGGAGT     480

TTGCAGACTC TCTGGGCATC CCCTTCTTGG AGACAGCGC CAAGAATGCC ACCAATGTCG      540

AGCAGGCGTT CATGACCATG GCTGCTGAAA TCAAAAAGCG GATGGGGCCT GGAGCAGCCT     600

CTGGGGGCGA GCGGCCCAAT CTCAAGATCG ACAGCACCCC TGTAAAGCCG GCTGGCGGTG     660

GCTGTTGCTA GGAGGGGCAC ATGGAGTGGG ACAGGAGGGG GCACCTTCTC CAGATGATGT     720

CCCTGGAGGG GGCAGGAGGT ACCTCCCTCT CCCTCTCCTG GGGCATTTGA GTCTGTGGCT     780

TTGGGGTGTC CTGGGCTCCC CATCTCCTTC TGGCCCATCT GCCTGCTGCC CTGAGCCCCG     840

GTTCTGTCAG GGTCCCTAAA GGAGGACACT CAGGGCCTGT GGCCAGGCAG GGCGGAAGCC     900

TGCTGTGCTG TTGCCTCTAG GTGAC                                          925
```

(2) INFORMATION FOR SEQ ID NO:5:

(i) SEQUENCE CHARACTERISTICS:
        (A) LENGTH: 221 amino acids
        (B) TYPE: amino acid
        (C) STRANDEDNESS: single
        (D) TOPOLOGY: linear (vii) IMMEDIATE SOURCE:
        (A) LIBRARY: UTRSNOT16
        (B) CLONE: 3400003

(xi) SEQUENCE DESCRIPTION: SEQ ID NO:5:

```
Met Ser Asp Ser Glu Glu Ser Gln Asp Arg Gln Leu Lys Ile Val
  1               5                  10                  15

Val Leu Gly Asp Gly Ala Ser Gly Lys Thr Ser Leu Thr Thr Cys Phe
             20                  25                  30

Ala Gln Glu Thr Phe Gly Lys Gln Tyr Lys Gln Thr Ile Gly Leu Asp
         35                  40                  45

Phe Phe Leu Arg Arg Ile Thr Leu Pro Gly Asn Leu Asn Val Thr Leu
 50                  55                  60

Gln Ile Trp Asp Ile Gly Gly Gln Thr Ile Gly Gly Lys Met Leu Asp
 65                  70                  75                  80

Lys Tyr Ile Tyr Gly Ala Gln Gly Val Leu Leu Val Tyr Asp Ile Thr
                 85                  90                  95

Asn Tyr Gln Ser Phe Glu Asn Leu Glu Asp Trp Tyr Thr Val Val Lys
            100                 105                 110

Lys Val Ser Glu Glu Ser Glu Thr Gln Pro Leu Val Ala Leu Val Gly
            115                 120                 125

Asn Lys Ile Asp Leu Glu His Met Arg Thr Ile Lys Pro Glu Lys His
    130                 135                 140

Leu Arg Phe Cys Gln Glu Asn Gly Phe Asn Ser His Phe Val Ser Ala
145                 150                 155                 160

Lys Ala Arg Asp Ser Val Phe Leu Cys Phe Gln Lys Val Val Ala Glu
                165                 170                 175

Ile Leu Gly Ile Lys Leu Asn Lys Ala Glu Ile Glu Gln Ser Gln Arg
            180                 185                 190

Val Val Lys Ala Asp Ile Val Asn Tyr Asn Gln Glu Pro Met Ala Arg
            195                 200                 205

Ala Val Asn Pro Ser Arg Ser Ser Val Cys Ala Val Gly
            210                 215                 220

(2) INFORMATION FOR SEQ ID NO:6:

(i) SEQUENCE CHARACTERISTICS:
        (A) LENGTH: 2713 base pairs
        (B) TYPE: nucleic acid
        (C) STRANDEDNESS: single
        (D) TOPOLOGY: linear (xi) SEQUENCE DESCRIPTION: SEQ ID NO:6:

GGGAGGTGGG CAAGATGGCG CTTGCCGAGT GATTCTCCTC GAATACCTCC TGCCGGCGCG      60

GAGACACCGG GGCGGGGGTC CTGCCGCAAC TACCTCCCTT CCTCCTCTCC CCCGCCCCCG     120

GAGCCTTCAT CCTTCCCTTC CCCCCCCACC TCGAGGGGCG GGCCTGGTTC CCGGGACACC     180

ATGTCGGACT CTGAGGAGGA GAGCCAGGAC CGGCAACTGA AAATCGTCGT GCTGGGGGAC     240

GGCGCCTCCG GGAAGACCTC CTTAACTACG TGTTTTGCTC AAGAAACTTT TGGGAAACAG     300

TACAAACAAA CTATAGGACT GGATTTCTTT TTGAGAAGGA TAACATTGCC AGGAAACTTG     360

AATGTTACCC TTCAAATTTG GGATATAGGA GGGCAGACAA TAGGAGGCAA ATGTTGGAT      420

AAATATATCT ATGGAGCACA GGGAGTCCTC TTGGTATATG ATATTACAAA TTATCAAAGC     480

TTTGAGAATT TAGAAGATTG GTATACTGTG GTGAAGAAAG TGAGCGAGGA GTCAGAAACT     540

CAGCCACTGG TTGCCTTGGT AGGCAATAAA ATTGATTTGG AGCATATGCG AACAATAAAA     600

CCTGAAAAAC ACTTACGGTT TTGCCAGGAA AATGGTTTTA ATAGCCACTT TGTTTCAGCC     660

AAGGCAAGAG ACTCTGTCTT CCTGTGTTTT CAAAAGGTTG TTGCTGAAAT CCTTGGAATC     720

AAATTAAACA AAGCAGAAAT AGAACAGTCA CAGAGGGTGG TAAAGGCAGA TATTGTAAAC     780
```

```
TACAACCAGG AACCTATGGC AAGAGCTGTT AACCCTTCTA GAAGCTCTGT GTGTGCAGTT      840

GGGTGAGCTC ATTTTTCCAT TGTGTTGATA GTTTTGGCTG CCCTTCACCT CTGGGTGTGT      900

CTGAGAACTT CTAAGAACTT GTTTTATCAG TGACCATCTC TGTAGTTCAG TTAACACTTT      960

CCTCCGAACT TGCTTCATCT TTAAGTGTTC CTCCCAACCG CAGGCATGTA CTTGGGTTCA     1020

AAAGAATTCA ACTTTGGGAC CACACACTTT GCATTCAAAC TGGAAGTCTC ATTCTCTGGA     1080

ATTAGACTGT TTCATTGAAA AAGAATGGTG TCCGGCCAGG CGCGGTGGCT CATGCCTGTA     1140

ATCCCAGCAC TTTGGGAGGC CGAGGCGGGT GGATCACCTG AGGTCAGGAG TTCGAGACCA     1200

GCCTGGCCAA CATGGTGAAA CCCCTGTCTC TACTAAAAAT ACAAAAAAAT TAGCTGGGCG     1260

CGGTGGCGCA TGCCTGTAAT CCCAGCTACT CAGGAGGCTG AGGCAGGAGA ATCACTTGAA     1320

CCCGGGAGGC AGAGGTTGCA GTGAGCCGAG ATCATGCCAT TGCACTCCAG CCTGGGTGAC     1380

AGAGCGAGAC TCCATCTCAA AAAAATAAA TAAATAAATT ATGAATGAGT ATTTTCTAGA     1440

AATTCAACTT GCTAAGCCTG TAATACTTAA GGGTAGTTTA TCTAGATACA GTACTTTCTT     1500

CCCTGATAAG TAGTATCATT GGAGCCCTTA GGTATAGGAG AAGAGGAAGA AGTTTAAAAA     1560

GTGTAAGTGG GCCGGGCGTG GTGGCTCATG CCTGTAATCC CAGCACTTTG GGAGGCCGAG     1620

GCGGGCAGAT CACAAGGTCA GGAGATCGAG ACCATCCTGG CCAAGATGGT GAAACCCCGT     1680

CTCTACTAAA AATACAAAAT TAGCCGGCCG TGGTGGCTCA CACCTGTAAT CCCAGCTACT     1740

TGGGAGGCTG AGGCAGGAGA ATCACTTGAG GTCAGGAGTT TGAGACCAGC CTGGCCAACG     1800

TGGTGAAACC CTGTCTCTAC TAAAAATACA AAAACTAGGC CAGGCGCGGG TGGCACGCCT     1860

GTAATCTCAG CACTTTGGGA GGCCGAGGCA GGTGGATCAC CTGAGGTCAG GAGTTCAAGA     1920

CCAGCCTGGC CAACATGGTG AAACCCCACC TCTACTAAAA ATACAAAAAT TAGCCAGGCA     1980

TGGTGGTGCA TGCCTGTAAT CCCAGCTACT TGGGAGGCTG AGGCAGGAGA ATTGCTTGAA     2040

CCCGGGAGCA GAGGTTGCAG TGAGCCGAGA TCATGCCACT GCACTCCAGC CTGGGTGACA     2100

GAGCGAGACT CCATTTCAAA AAAAGAACT ACAAGTTCTG ATTCCGGACT CCCAGATGTG     2160

AGTTTTAATC TCCTCTCCAC TGATTGATCC TGACTAATCA CTAGCCCCCT GTGCCCAATT     2220

TCAACAGTAT GCTGGAGTCA AATCTGAACC CCAAACTATG CCCTCTTAAG GGGGGTCCCT     2280

CTGGGATGCC AACATGCATT CACTTCTTCA CCTGGCTAGG CATTCCATGA GTATTCACAT     2340

TGTAGTCACT CCCCTAGGGC TATGCCCAGG AGTTAGTACT TTCCTACCAC TTGGTGATCT     2400

TGAGTGAGTT TTGGATGTCC TCAATGGGTC CTGAGATGAG TCAGAGGAGA GCTAGAGTTG     2460

GGAACTGATC ACCAGTGGCC CCCCCAGTCC TCAGCTCTTG AAGGAAAGGG AATGAATTGC     2520

TCTGGCCATT TGCATCTGTG CGAAGGATCG AACAAAGCCA CTTTCTACAA TGCAACCCTG     2580

TCCGACGGCC CCCTTCCCAA AGCTGCCTGC AACTTTCAAC CCCGNTGAAT GGACTTTGGA     2640

ACTTGGGACA GAGGCAAAGA CTTAAATGAG GNGCCAAAGN AATGTCGGGT CCATTACCAA     2700

ATTAGGAGGG TNG                                                       2713
```

(2) INFORMATION FOR SEQ ID NO:7:

(i) SEQUENCE CHARACTERISTICS:
        (A) LENGTH: 203 amino acids
        (B) TYPE: amino acid
        (C) STRANDEDNESS: single
        (D) TOPOLOGY: linear (vii) IMMEDIATE SOURCE:
        (A) LIBRARY: GenBank
        (B) CLONE: 438164

(xi) SEQUENCE DESCRIPTION: SEQ ID NO:7:

```
Met Ser Gly Gln Arg Val Asp Val Lys Val Met Leu Gly Lys Glu
1               5                  10                 15

Tyr Val Gly Lys Thr Ser Leu Val Glu Arg Tyr Val His Asp Arg Phe
                20                  25                 30

Leu Val Gly Pro Tyr Gln Asn Thr Ile Gly Ala Ala Phe Val Ala Lys
            35                  40                 45

Val Met Cys Val Gly Asp Arg Thr Val Thr Leu Gly Ile Trp Asp Thr
    50                  55                  60

Ala Gly Ser Glu Arg Tyr Glu Ala Met Ser Arg Ile Tyr Tyr Arg Gly
65                  70                  75                  80

Ala Lys Ala Ala Ile Val Cys Tyr Asp Leu Thr Asp Ser Ser Ser Phe
                85                  90                  95

Glu Arg Ala Lys Phe Trp Val Lys Glu Leu Arg Ser Leu Glu Glu Gly
                100                 105                110

Cys Gln Ile Tyr Leu Cys Gly Thr Lys Ser Asp Leu Leu Glu Glu Asp
                115                 120                125

Arg Arg Arg Arg Val Asp Phe His Asp Val Gln Asp Tyr Ala Asp
    130                 135                 140

Asn Ile Lys Ala Gln Leu Phe Glu Thr Ser Ser Lys Thr Gly Gln Ser
145                 150                 155                 160

Val Asp Glu Leu Phe Gln Lys Val Ala Glu Asp Tyr Val Ser Val Ala
                165                 170                 175

Ala Phe Gln Val Met Thr Glu Asp Lys Gly Val Asp Leu Ser Gln Lys
                180                 185                 190

Ala Asn Pro Tyr Phe Tyr Ser Cys Cys His His
                195                 200
```

(2) INFORMATION FOR SEQ ID NO:8:

(i) SEQUENCE CHARACTERISTICS:
       (A) LENGTH: 201 amino acids
       (B) TYPE: amino acid
       (C) STRANDEDNESS: single
       (D) TOPOLOGY: linear (vii) IMMEDIATE SOURCE:
       (A) LIBRARY: GenBank
       (B) CLONE: 57006

(xi) SEQUENCE DESCRIPTION: SEQ ID NO:8:

```
Met Asn Pro Glu Tyr Asp Tyr Leu Phe Lys Leu Leu Leu Ile Gly Asp
1               5                   10                 15

Ser Gly Val Gly Lys Ser Cys Leu Leu Leu Arg Phe Ala Asp Asp Thr
                20                  25                  30

Tyr Thr Glu Ser Tyr Ile Ser Thr Ile Gly Val Asp Phe Lys Ile Arg
            35                  40                  45

Thr Ile Glu Leu Asp Gly Lys Thr Ile Lys Leu Gln Ile Trp Asp Thr
    50                  55                  60

Ala Gly Gln Glu Arg Phe Arg Thr Val Thr Ser Ser Tyr Tyr Arg Gly
65                  70                  75                  80

Ala His Gly Ile Ile Val Val Tyr Asp Val Thr Asp Gln Glu Ser Tyr
                85                  90                  95

Ala Asn Val Lys Gln Trp Leu Gln Glu Ile Asp Arg Tyr Ala Ser Glu
                100                 105                 110

Asn Val Asn Lys Leu Leu Val Gly Asn Lys Ser Asp Leu Thr Thr Lys
```

```
            115                 120                 125
Lys Val Val Asp Asn Thr Thr Ala Lys Glu Phe Ala Asp Ser Leu Gly
    130                 135                 140

Val Pro Phe Leu Glu Thr Ser Ala Lys Asn Ala Thr Asn Val Glu Gln
145                 150                 155                 160

Ala Phe Met Thr Met Ala Ala Glu Ile Lys Lys Arg Met Gly Pro Gly
                165                 170                 175

Ala Ala Ser Gly Gly Glu Arg Pro Asn Leu Lys Ile Asp Ser Thr Pro
            180                 185                 190

Val Lys Ser Ala Ser Gly Gly Cys Cys
            195                 200
```

(2) INFORMATION FOR SEQ ID NO:9:

(i) SEQUENCE CHARACTERISTICS:
        (A) LENGTH: 221 amino acids
        (B) TYPE: amino acid
        (C) STRANDEDNESS: single
        (D) TOPOLOGY: linear (vii) IMMEDIATE SOURCE:
        (A) LIBRARY: GenBank
        (B) CLONE: 1154901

(xi) SEQUENCE DESCRIPTION: SEQ ID NO:9:

```
Met Ser Asp Ser Glu Glu Ser Gln Asp Arg Gln Leu Lys Ile Val
1               5                   10                  15

Val Leu Gly Asp Gly Thr Ser Gly Lys Thr Ser Leu Ala Thr Cys Phe
                20                  25                  30

Ala Gln Glu Thr Phe Gly Lys Gln Tyr Lys Gln Thr Ile Gly Leu Asp
            35                  40                  45

Phe Phe Leu Arg Arg Ile Thr Leu Pro Gly Asn Leu Asn Val Thr Leu
50                  55                  60

Gln Val Trp Asp Ile Gly Gly Gln Thr Ile Gly Gly Lys Met Leu Asp
65                  70                  75                  80

Lys Tyr Ile Tyr Gly Ala Gln Gly Ile Leu Leu Val Tyr Asp Ile Thr
                85                  90                  95

Asn Tyr Gln Ser Phe Glu Asn Leu Glu Asp Trp Tyr Ser Val Val Lys
                100                 105                 110

Thr Val Ser Glu Glu Ser Glu Thr Gln Pro Leu Val Ala Leu Val Gly
            115                 120                 125

Asn Lys Ile Asp Leu Glu His Met Arg Thr Val Lys Pro Asp Lys His
            130                 135                 140

Leu Arg Phe Cys Gln Glu Asn Gly Phe Ser Ser His Phe Val Ser Ala
145                 150                 155                 160

Lys Thr Gly Asp Ser Val Phe Leu Cys Phe Gln Lys Val Ala Ala Glu
                165                 170                 175

Ile Leu Gly Ile Lys Leu Asn Lys Ala Glu Ile Glu Gln Ser Gln Arg
            180                 185                 190

Val Val Lys Ala Asp Ile Val Asn Tyr Asn Gln Glu Pro Met Ser Arg
            195                 200                 205

Thr Val Asn Pro Pro Arg Ser Ser Met Cys Ala Val Gln
210                 215                 220
```